(12) United States Patent
Austin et al.

(10) Patent No.: US 12,151,075 B2
(45) Date of Patent: Nov. 26, 2024

(54) DEVICES AND SYSTEMS FOR PREPARING THERAPEUTIC PELLETS

(71) Applicant: AUSTIN MEDICAL VENTURES INC., Germantown, TN (US)

(72) Inventors: William Brian Austin, Germantown, TN (US); Edward J. McPherson, Bakersfield, CA (US); Andrew J. Wassef, Rancho Palos Verdes, CA (US); Scott P. Noel, Germantown, TN (US); Stephen T. Miller, Scotts Valley, CA (US)

(73) Assignee: Austin Medical Ventures Inc., Germantown, TN (US)

( * ) Notice: Subject to any disclaimer, the term of this patent is extended or adjusted under 35 U.S.C. 154(b) by 0 days.

(21) Appl. No.: 18/531,447

(22) Filed: Dec. 6, 2023

(65) Prior Publication Data

US 2024/0100312 A1    Mar. 28, 2024

Related U.S. Application Data

(62) Division of application No. 18/054,449, filed on Nov. 10, 2022.

(60) Provisional application No. 63/278,269, filed on Nov. 11, 2021.

(51) Int. Cl.
*A61M 37/00*    (2006.01)
*A61J 3/00*    (2006.01)

(52) U.S. Cl.
CPC ............ *A61M 37/0069* (2013.01); *A61J 3/00* (2013.01)

(58) Field of Classification Search
CPC .......... A61M 37/0069; A61J 3/00; A61J 3/06; B65D 75/367; B65D 75/323; F25C 1/243
See application file for complete search history.

(56) References Cited

U.S. PATENT DOCUMENTS

| 534,633 | A | * | 2/1895 | Coleman | F25C 1/24 |
| | | | | | D7/672 |
| 2,053,711 | A | * | 9/1936 | Glomb | F25C 1/24 |
| | | | | | 249/120 |
| 2,433,211 | A | * | 12/1947 | Gits | F25C 1/243 |
| | | | | | 206/559 |
| 2,505,947 | A | * | 5/1950 | De Brocke | F25C 1/243 |
| | | | | | 426/104 |
| 3,483,908 | A | * | 12/1969 | Donovan | B65D 1/40 |
| | | | | | 220/675 |
| 3,844,525 | A | * | 10/1974 | Parmett | F25C 1/243 |
| | | | | | 229/406 |

(Continued)

FOREIGN PATENT DOCUMENTS

| EP | 2594231 A1 | 5/2013 |
| EP | 3058899 A2 | 8/2016 |

*Primary Examiner* — Emmanuel S Luk
(74) *Attorney, Agent, or Firm* — Haynes and Boone, LLP

(57) ABSTRACT

Devices and methods for mixing and preparing therapeutic pellets are described. In one aspect, the present disclosure may include a medical device for mixing and preparing pharmaceuticals. The medical device may include a body sized and shaped to be supported by a human hand. The body may be elastically flexible between a relaxed shape and a flexed shape. In the relaxed shape, the body may form a basin and may be shaped and sized to receive a vessel for mixing or forming the therapeutic pellets. In the flexed shape, the bowl may be configured for controlled pouring of the therapeutic pellets.

14 Claims, 16 Drawing Sheets

(56) References Cited

U.S. PATENT DOCUMENTS

| | | | | |
|---|---|---|---|---|
| 4,038,937 | A * | 8/1977 | Moe | A61J 7/0084 D11/158 |
| 4,147,324 | A * | 4/1979 | Walter | F41J 1/01 249/126 |
| 4,222,547 | A * | 9/1980 | Lalonde | F25C 1/243 249/141 |
| 4,547,143 | A * | 10/1985 | Cerreta | A23G 3/0273 426/512 |
| 4,693,371 | A * | 9/1987 | Malpass | B65D 1/36 206/561 |
| 4,887,790 | A * | 12/1989 | Wilkinson | A61J 3/06 220/507 |
| 5,069,261 | A | 12/1991 | Ji | |
| 5,397,097 | A * | 3/1995 | Dale | F25C 1/243 D15/90 |
| 5,437,406 | A | 8/1995 | Gordon | |
| 5,511,684 | A * | 4/1996 | Weaver, Jr. | B65D 25/38 206/505 |
| 5,549,204 | A * | 8/1996 | Toren | B65D 75/327 220/4.23 |
| 5,830,379 | A * | 11/1998 | Tunzi | F25C 1/243 249/126 |
| 6,793,193 | B2 * | 9/2004 | de Groote | A47J 43/20 99/426 |
| 7,014,162 | B2 * | 3/2006 | Lion | F25C 1/24 249/126 |
| 8,883,063 | B2 | 11/2014 | Laycock | |
| 10,390,954 | B2 | 8/2019 | Colclough | |
| 10,588,748 | B2 | 3/2020 | Colclough | |
| 11,021,294 | B2 * | 6/2021 | Hogan | B65D 17/401 |
| 11,259,529 | B2 * | 3/2022 | Fletcher | A21D 13/80 |
| 2003/0213721 | A1 * | 11/2003 | Jones | B65D 75/367 206/528 |
| 2004/0093835 | A1 * | 5/2004 | Siegel | B65D 75/323 53/558 |
| 2005/0051459 | A1 * | 3/2005 | Casanova | B65D 75/367 206/703 |
| 2005/0087472 | A1 * | 4/2005 | Elliott | B65D 77/2032 206/528 |
| 2006/0289524 | A1 | 12/2006 | Ludwig | |
| 2007/0205132 | A1 * | 9/2007 | Bouthiette | B65D 75/327 206/538 |
| 2008/0223861 | A1 | 9/2008 | Agresta | |
| 2009/0050784 | A1 * | 2/2009 | Slappay | F25C 1/24 249/203 |
| 2010/0012531 | A1 | 1/2010 | Steele | |
| 2010/0155271 | A1 * | 6/2010 | Hammerl | B65D 75/323 53/425 |
| 2012/0037618 | A1 | 2/2012 | Perez | |
| 2013/0082050 | A1 * | 4/2013 | Wiebold | B65D 75/323 220/4.24 |
| 2013/0160408 | A1 * | 6/2013 | Neff | B65D 75/323 206/532 |
| 2014/0116264 | A1 * | 5/2014 | Hauser | A21B 3/132 99/426 |
| 2014/0245698 | A1 | 9/2014 | Steele | |
| 2015/0097026 | A1 | 4/2015 | Lu | |
| 2016/0235534 | A1 | 8/2016 | Colclough | |
| 2017/0020673 | A1 | 1/2017 | Colclough | |
| 2018/0194528 | A1 | 7/2018 | Franca | |
| 2019/0270546 | A1 | 9/2019 | Finell | |
| 2019/0337665 | A1 | 11/2019 | Lu | |
| 2020/0284489 | A1 | 9/2020 | Finell | |
| 2020/0307885 | A1 | 10/2020 | Mazzola | |
| 2020/0348066 | A1 * | 11/2020 | Victorio Lima | F25C 1/24 |
| 2021/0300618 | A1 | 9/2021 | Lu | |
| 2022/0017731 | A1 | 1/2022 | Soibel | |

\* cited by examiner

DEVICES AND SYSTEMS FOR PREPARING THERAPEUTIC PELLETS

CROSS-REFERENCE TO RELATED APPLICATIONS

The present application is a Divisional Application of U.S. patent application Ser. No. 18/054,449, filed Nov. 10, 2022, and claims priority from and the benefit of the filing date of U.S. Provisional Patent Application Ser. No. 63/278,269, filed on Nov. 11, 2021, the entirety of which is incorporated by reference herein.

FIELD OF THE INVENTION

The invention is related to the field of preparing therapeutic pellets. In particular, therapeutic pellets that may be prepared during orthopedic surgery.

BACKGROUND

Therapeutic pellets may be used during surgery to stabilize the surgical site and/or deliver therapeutics to the surgical site. For example, therapeutic pellets may be used during orthopedic surgery and may provide a scaffold for bone ingrowth, which may include bone growth factors or other characteristics to enhance bone growth. In some cases, the therapeutic pellets may deliver antibiotics to the surgical site to prevent infection. In some applications, the therapeutic pellets may carry bone cements, including calcium-based bone cements such as calcium sulfates and/or calcium phosphates. Such cements may be delivered to a wound or surgical site to facilitate healing, fill bony defects, and/or control infection.

These therapeutic pellets may be created in the operating room during surgery. For example, the surgeon may mix a powder with a liquid to make a paste, form the paste into shapes, often with the help of a mold, and let the paste cure to form hardened pellets. The surgeon may then deliver the pellets to the surgical site. Easing the process of forming the pellets and delivering them to the surgical site can make the surgery go more smoothly. Thus, improved systems for forming and delivering pellets is needed.

BRIEF SUMMARY OF THE INVENTION

The present disclosure provides devices, systems, and methods for forming therapeutic pellets. Therapeutic pellets can be spherical, cylindrical, bullet-shaped, tablet-shaped, or any other suitable shape. In some embodiments, pellets can be formed by providing a portion of the mixed paste and spreading the mixed paste into a flexible mold that has cavities in the desired shape. Once the paste has cured in the mold, the pellets are removed from the mold by flexing the mold and then placed into the patient.

In one aspect of the present disclosure, a medical device for preparation and introduction of therapeutic pellets to a surgical site is provided. The medical device may include a body sized and shaped to be supported by a human hand. The body may be elastically flexible between a relaxed shape and a flexed shape. In the relaxed shape the body may form a basin being shaped and sized to receive a vessel for mixing or forming the therapeutic pellets. In the flexed shape the body may be configured for controlled pouring of the therapeutic pellets.

In some embodiments, the body of the medical device may include a flexible-bowl-shaped body. The flexible bowl-shaped body may include an elastomeric material and may be configured to form a releasable interference fit with an exterior surface of a bowl when the bowl is disposed within the basin. The bowl-shaped body may include a rim along the top of the bowl-shaped body and a recess defined in the bowl-shaped body along a portion of the rim. The bowl-shaped body may be configured to fold inward such that opposing sides of the rim are closer to one another such that the recess forms an opening for dispensing the therapeutic pellets.

In some embodiments, the recess may be configured to form a spout for dispensing the therapeutic pellets when the flexible bowl-shaped body is folded. In some embodiments, the flexible bowl-shaped body may be configured to be folded by one hand of a user. In some embodiments, the bowl-shaped body may further include a second recess defined in the flexible bowl-shaped body along a second portion of the rim opposite the recess. In some embodiments, the flexible bowl-shaped body further include a tab extending from the second recess, where the tab is configured to prevent rotation of the flexible bowl-shaped body relative to the bowl. In some embodiments, the tab may be configured to engage with a corresponding tab in the bowl. In some embodiments, the opening for dispensing the therapeutic pellets may be sized to limit a number of therapeutic pellets that can be poured out of the flexible bowl-shaped body at once.

In one aspect, a kit for therapeutic pellets may be provided. The kit may include a bowl containing a powder material, a liquid container containing liquid configured to mix and react with the powder material to form the therapeutic pellets, and a bowl-shaped body according to one or more of the embodiments of the present disclosure. The bowl-shaped body may be disposed over an exterior surface of the bowl.

In some aspects, the medical device may include a flat surface and two or more raised edges which, together with the flat surface, form the basin. The basin may be configured to receive a flexible mold for forming and curing the therapeutic pellets.

Some embodiments of the present disclosure include a backer board. The backer board may include a flat surface and two or more raised edges extending upward from the flat surface. The backer board may be formed of a first material comprising a first rigidity. The backer board may be shaped to support an elastomeric mold having a second rigidity. The first rigidity of the first material may be greater than the second rigidity of the elastomeric mold. The backer board may be configured to be supportable by one hand of a user.

In some embodiments, the backer board may include a relief configured to facilitate bending of the backer board about the relief. In some embodiments, there may be a first cutout at a corner of the backer board and the relief may be oriented toward the first cutout. In some embodiments, the relief may have a first end disposed proximal to the first cutout and a second end at a side of the backer board. In some embodiments, there may be a second cutout located at the second end of the relief on the side of the backer board. In some embodiments, the relief may be thinner than the flat surface. In some embodiments, the backer board may have a width in the range of 2 to 6 inches and a length in the range of 3 to 12 inches.

In some aspects, a kit for therapeutic pellets may be provided. The kit may include a backer board according to one or more aspects of the present disclosure and an elastomeric mold defining one or more cavities. The backer board may be sized and shaped to receive and support the elastomeric mold.

In some embodiments, the two or more raised edges of the backer board may be configured to fit around a perimeter of the elastomeric mold. In some embodiments, the elastomeric mold may be formed of a silicone rubber and the backer board may be formed of a material that is more rigid that the silicone rubber. In some embodiments, the cavities may be configured to hold a paste during a curing process to form the therapeutic pellets. In some embodiments, the mold may have a first set of cavities and a second set of cavities, where a volume of each cavity in the first set of cavities is greater than a volume of each cavity in the second set of cavities. In some embodiments, the mold comprises a first height at the first set of cavities and a second height at the second set of cavities, where the first height is greater than the second height. The mold may have a first depth for each of the first set of cavities and a second depth for each of the second set of cavities, where the first height is proportional to the first depth and the second height is proportional to the second depth. In some embodiments, the first height may be in a range of 1.25 to 1.75 times the first depth and the second height may be in a range of 1.25 to 1.75 times the second depth.

According to some embodiments of the present invention, a kit for therapeutic pellets may be provided. The kit may comprise a bowl containing a powder material, a liquid container containing liquid configured to mix with the powder material to form the therapeutic pellets, and a flexible cover removably disposed over an exterior surface of the bowl in a manner that allows a user to hold the bowl during mixing by gripping the flexible cover. The flexible cover may be removable from the bowl and flexible to form a pouring spout usable to introduce the therapeutic pellets to a surgical site.

In some embodiments, the kit may further include a relatively more rigid backer board and a relatively less rigid mold having one or more cavities. The backer board may be shaped to support the less rigid mold. In some embodiments, the relatively more rigid backer board may include a relief configured to facilitate bending of the backer board to form a spout.

Some embodiments of the present disclosure may include a method of forming therapeutic pellets. The method may include the steps of: mixing a liquid from a liquid container with a powder material to form a mixture in a bowl having a removable, flexible cover; introducing the mixture to a flexible mold disposed on a backer board to form the therapeutic pellets, wherein the backer board is more rigid than the flexible mold; ejecting the therapeutic pellets from the flexible mold into the backer board; and deforming the backer board to form a spout.

In some embodiments, the method may also comprise the step of delivering the therapeutic pellets from the backer board to a surgical site. The backer board may include a relief to facilitate bending. In some embodiments, the method may also comprise the steps of: removing the flexible cover from the bowl; folding the flexible cover to form a spout for delivering the therapeutic pellets; and delivering the therapeutic pellets from the spout to a surgical site.

Although described with respect to bone cement, it will be understood that the present disclosure contemplates other types of cements, pellets, pastes, and/or materials and applications. For example, the devices and methods described herein may be suitable for forming antibiotic pellets during a curing process to form the therapeutic pellets.

These and other objects, features and advantages of this invention will become apparent from the following detailed description of the various aspects and principles of the invention taken in conjunction with the accompanying drawings.

BRIEF DESCRIPTION OF THE DRAWINGS

The accompanying drawings, which are incorporated in and constitute a part of the specification, illustrate embodiments of the invention and, together with the detailed description herein, serve to explain the principles of the invention. The drawings are only for purposes of illustrating examples and are not to be construed as limiting the invention. It is emphasized that, in accordance with the standard practice in the industry, various features are not drawn to scale. In fact, the dimensions of the various features may be arbitrarily increased or reduced for clarity of discussion.

DETAILED DESCRIPTION

Figure 1:
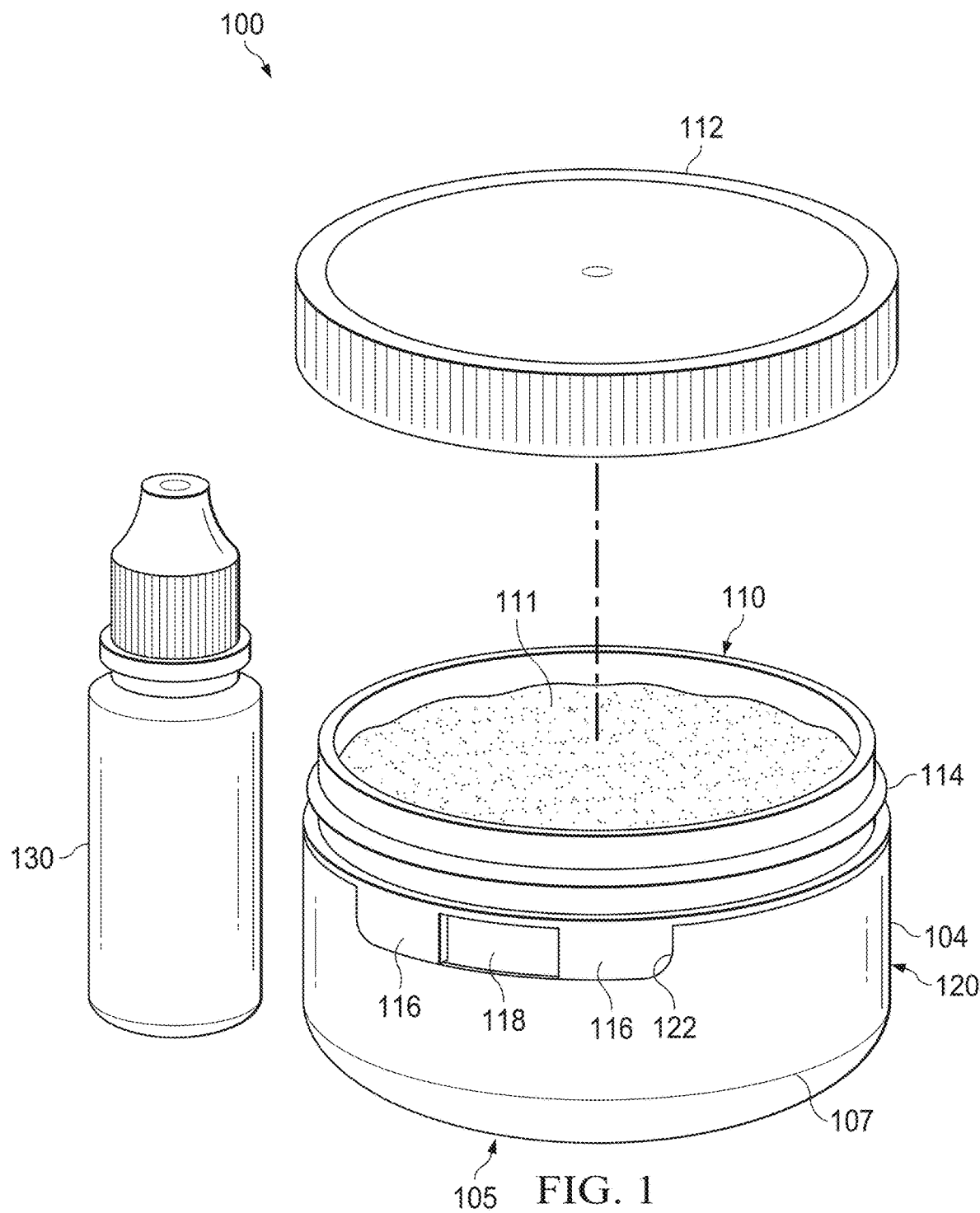
FIG. 1 shows a perspective view of a pellet preparation kit, according to aspects of the present disclosure.

For the purpose of promoting an understanding of the principles of the present disclosure, reference will now be made to the implementations illustrated in the drawings and specific language will be used to describe them. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In addition, this disclosure describes some elements or features in detail with respect to one or more implementations or figures, when those same elements or features appear in subsequent figures, without such a high level of detail. It is fully contemplated that the features, components, and/or steps described with respect to one or more implementations or figures may be combined with the features, components, and/or steps described with respect to other implementations or figures of the present disclosure. For simplicity, in some instances the same or similar reference numbers are used throughout the drawings to refer to the same or like parts.

As stated above, aspects of the present disclosure include devices, systems, and methods for forming therapeutic pellets. Therapeutic pellets can be formed by providing a portion of the mixed paste and spreading the mixed paste into a flexible mold that has cavities in the desired shape. In some embodiments, the user works the paste into the cavities of the mold, attempting to avoid wasting paste on the top or sides of the mold. Different tools can be used for mixing, spreading, and mold-filling of the paste. Even with these tools, preparing uniform pellets can be difficult, especially if the flexible mold is stretched or deformed while curing. Once the paste has cured in the mold, the pellets are removed from the mold by flexing the mold and then placed into the patient. The devices, systems, and methods described herein advantageously facilitate preparation and delivery of therapeutic pellets.

Figure 2:
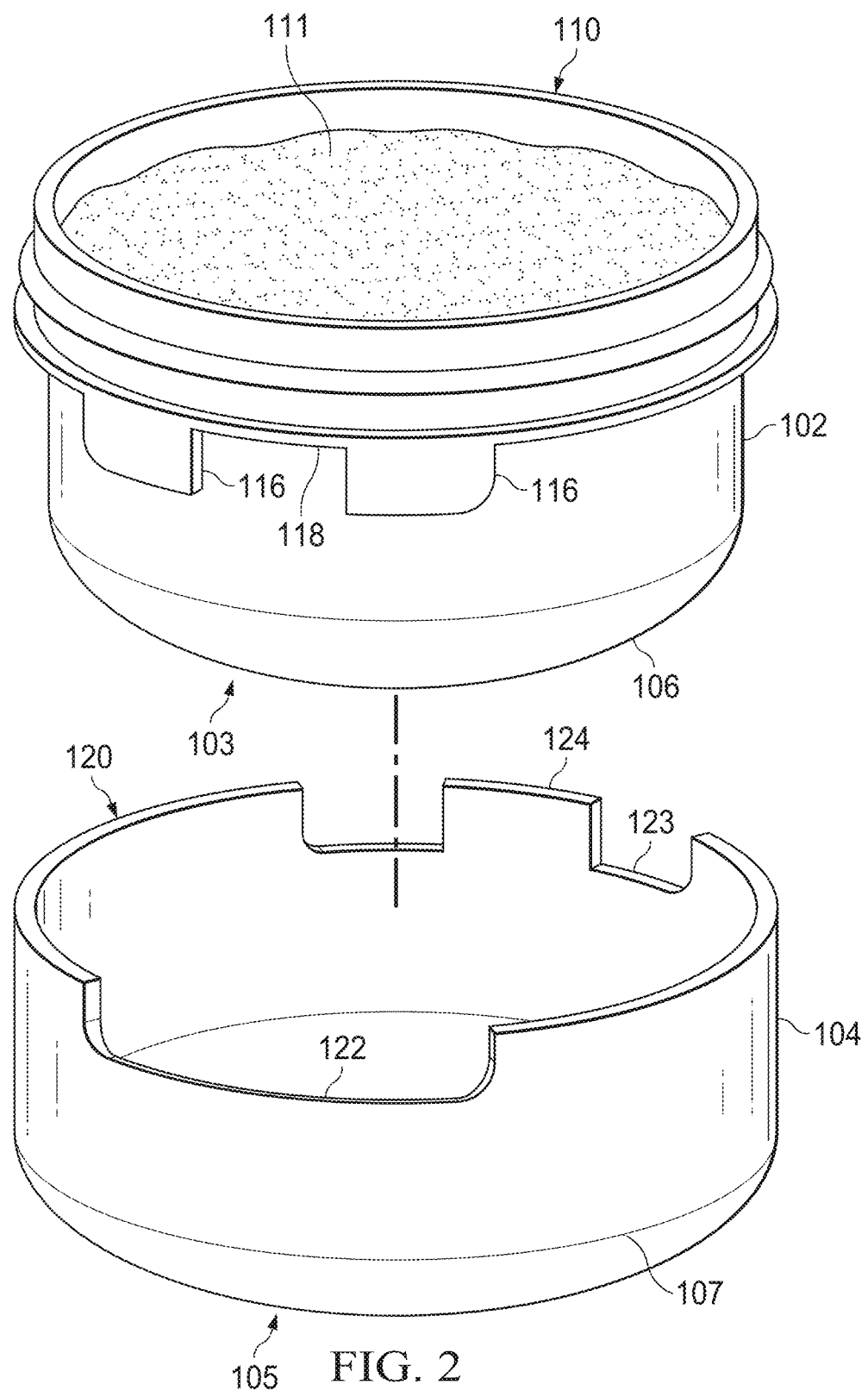
FIG. 2 shows a perspective view of the bowl and flexible cover of the pellet preparation kit shown in FIG. 1, according to aspects of the present disclosure.

FIG. 1 is a perspective view of a kit 100 for preparing or forming therapeutic pellets, according to an embodiment of the present disclosure. The kit 100 includes a flexible cover 120 that fits over a bowl 110. FIG. 2 is an exploded view of the cover 120 and the bowl 110 shown in FIG. 1. Referring to FIGS. 1 and 2, the flexible cover 120 may fit snugly over the bowl 110 such that the flexible cover 120 forms an interference fit with the bowl 110. The bowl 110 includes threads 114 to threadably engage with a lid 112 so that the bowl 110 can contain one or more of the components of the kit 100. In other words, the bowl 110 may double as packaging for the kit in addition to being used to mix the powder 111 and liquid 130 as described in more detail below. In some embodiments, the bowl 110 includes coupling features other than threads for coupling to the lid 112, such as tabs, latches, adhesives, and/or any other suitable coupling feature.

The cover 120 comprises a flexible material, such as for example only, an elastomeric material such as silicone rubber or a thermoplastic elastomer. These materials may have relatively high coefficients of friction when gripped by a user, enabling them to provide enhanced grip when the cover 120 is disposed over the bowl 110. The flexible material of the cover 120 may provide a better grip when the user is mixing the components together in the bowl 110 or scraping the paste out of the bowl. In embodiments where a lid 112 is included in the kit 100, the flexible material of the cover 120 may make it easier to open the lid 112. In some embodiments, the lid 112 is separate from, but attachable to the bowl 110. In some embodiments, the lid 112 may be hinged or otherwise connected to the bowl 110.

In some embodiments, the cover 120 closely matches the shape or outer profile of the bowl 110. By having a close match in shape, the flexible cover 120 can securely hold the bowl 110 using friction and/or suction. For example, the flexible cover 120 may form an interference fit with the bowl 110, and may be elastically stretched to receive the bowl therein. The bowl 110 may include one or more tabs 116 or slots that engage a pouring recess 122 formed in the cover 120. In the illustrated embodiment, the bowl 110 has two tabs 116 that are raised from the surface of the bowl 110 and there is a space 118 between the two tabs 116. The tabs 116 engage the sides of the pouring recess 122. The tabs 116 may help resist rotation of the bowl 110 relative to the cover 120.

The bowl 110 may also have one or more tabs or slots opposing the tabs 116 for engaging the pouring recess 122. These tabs may be configured to engage an opposing recess 123 of the cover 120. The opposing recess 123 may have a tab 124 or slot that extends from the recess 123 to resist the rotation of the bowl 110 relative to the cover 120. In the illustrated embodiment, the bowl 110 has two tabs 116 that are raised from the surface of the bowl 110. Not shown are two similar tabs 116 on the opposite side of the bowl. There is a space 118 between the tabs 116 for fitting the corresponding tab 124 of the cover 120. The tab 124 of the cover 120 may engage the tabs 116 on the bowl 110 to prevent rotation of the cover 120 relative to the bowl 110. In some embodiments, the bowl 110 may include pre-packaged powder 111 used to form the pellets. The lid 112 may be affixed to the bowl 110 to seal the powder 111 within the bowl 110 for simple packaging, delivery to, and storage at a use-site, such as a hospital.

In some embodiments, the kit 100 further includes a liquid 130 configured to be mixed with the powder 111 contained in the bowl 110 to create the pellet material. In some embodiments, the liquid 130 includes water and the powder 111 is a calcium-based powder. The liquid 130 may be mixed with the powder 111 in the bowl 110 to form a paste. In some embodiments, the liquid 130 and powder 111 may be mixed to form a mixture that is more liquid or more solid than a paste. In some embodiments, the liquid 130 may include catalysts or retardants that control the speed of the curing of the pellets as discussed in more detail below. The combination of the liquid 130 and the powder 111 may be configured to cure and/or harden to form the pellets. As explained below, the paste formed of the powder 111 and the liquid 130 can be worked into a flexible mold or mat having cavities that will define the shape of the pellets. In some embodiments, the liquid 130 is provided in any appropriate container, including, for example, a dropper, a vial, a second bowl with a lid, or any other appropriate container.

The bowl 110 and the body 126 of the cover 120 may be relatively cylindrical having generally straight sides 102, 104 connected to a flat or rounded bottom 103, 105. The sides 102, 104 and bottom 103, 105 may be connected by rounded edges 106, 107. The slightly rounded bottom 103, 105 may allow the bowl 110 and cover 120 to be placed on a flat surface with minimal wobbling while making it easier for mixing. The rounded edges 106, 107 may also make it easier to mix by preventing the buildup of compacted material in the corners. In some embodiments, the body 126 of the cover 120 may be generally semi-spherical. In some embodiments, the bowl 110 may not be rounded, but may instead be rectangular or cubic. Thus, the cover 120 may also be rectangular or cubic to match the shape of the bowl 110. The bowl 110 may be any other appropriate shape. For example, the bowl 110 may be hexagonal, ovate, or triangular. Similarly, the cover 120 may also be any shape to match the shape of the bowl 110, including hexagonal, ovate, or triangular.

In the illustrated embodiment, the width and length of the bowl 110 are larger than the height. However, the height may be larger than the width and length. In some embodiments, the width and length may be the same or may be different.

Figure 3:
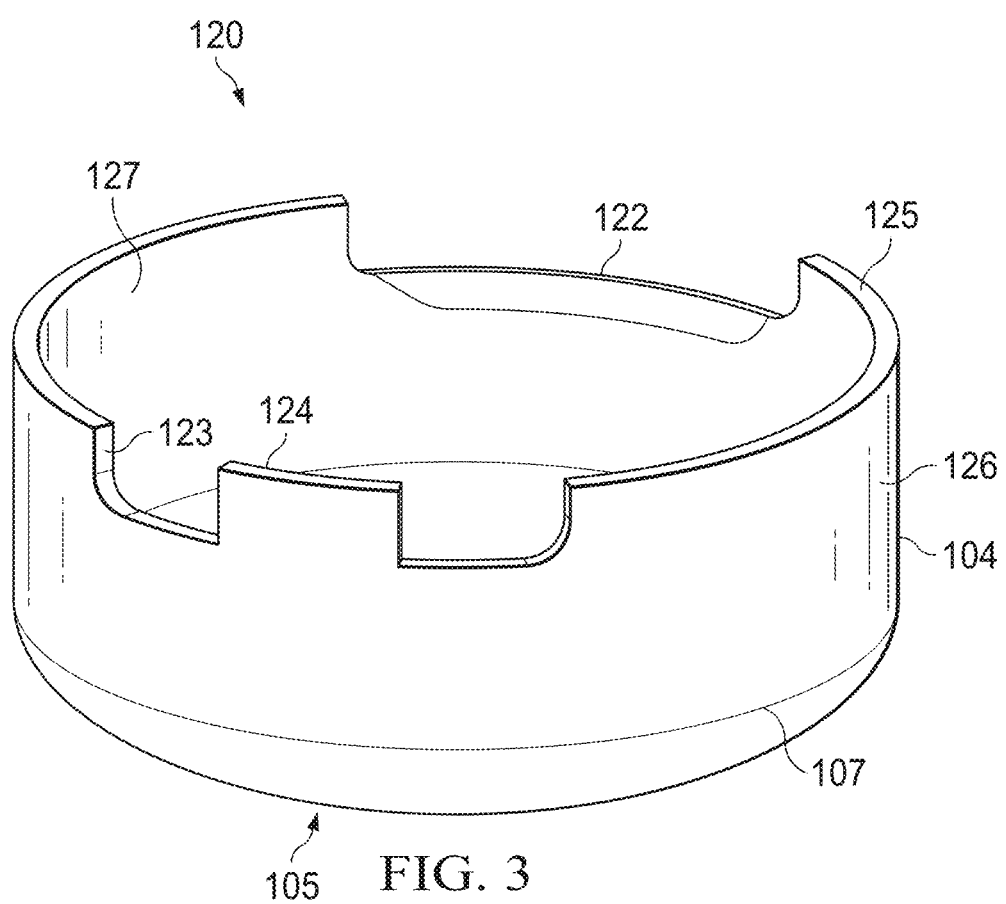
FIG. 3 shows a perspective view of the flexible cover of the pellet preparation kit shown in FIG. 1, according to aspects of the present disclosure.

FIG. 3 is a perspective view of the cover 120. The cover 120 may include, or be formed of, a flexible material, such as silicone, rubber, latex, a thermoplastic elastomer, and/or any other suitable type of material. The material of the cover 120 may be chosen so that the cover 120 can be folded with pressure or force while maintaining its shape in the absence of a pressure or force. The cover 120 comprises a bowl-like shape corresponding to the shape of the bowl 110. The body 126 of the cover 120 has an inner surface 127 which is configured to contact an outer surface of the bowl 110. The shape of the cover 120 may form a basin that holds the bowl 110. There is a rim 125 along the top of the body 126. The cover 120 includes a pouring recess 122 formed in the cover 120 along the rim 125, which can aid in the pouring or funneling of the cured pellets into the surgical site, as explained further below. In other embodiments, the cured pellets may be delivered to a wound, and not to a surgical site.

The cover 120 is flexible such that it may be squeezed, flexed, or folded along an axis to form a lemon-like shape, where the pouring recess 122 forms an opening on one end of the lemon-like shape of the folded cover 120. The pouring recess 122 is configured to form a spout to provide for a more controlled delivery of the pellets from the cover 120. In some embodiments, there may be an extension that extends outward from the bottom of the pouring recess 122. When the cover 120 is folded, the extension may be shaped around to form a spout for the opening formed by the pouring recess 122 to improve control when pouring pellets out of the cover 120. In the illustrated embodiment, the pouring recess 122 is U-shaped, where the width of the pouring recess 122 is larger than the height. In some embodiments, the pouring recess 122 is U-shaped with a height that is larger than the width. In some embodiments, the pouring recess 122 is V-shaped, rectangular, semi-circular or any other appropriate shape. In some embodiments, the cover 120 further includes an opposing recess 123, which is aligned with the pouring recess 122. The folding axis of the cover 120 may pass through both recesses 122, 123. Thus, the opposing recess 123 may allow the cover 120 to fold more easily.

In some embodiments, the opposing recess 123 includes a tab 124 that extends into the open space of the recess 123. The tab 124 may extend from any part of the recess 123, including, for example, the bottom of the recess (as illustrated) or the sides of the recess 123. As discussed previously, the tab 124 may align with the tabs 116 and the opening 118 of the bowl 110 so that the cover 120 is properly aligned with the bowl 110 and is prevented from rotating relative to the bowl 110. In some embodiments, when the cover 120 is folded in half, the tab 124 may be configured to increase the size of the opening formed by the pouring recess 122. In some embodiments, the tab 124 may be configured to reduce the size of the opening. In other embodiments, the tab 124 may be configured so that it does not interfere with the folding of the cover 120.

The cover 120 may be sized and shaped so that it can be held in one hand. For example, the cover may be in the range of 2 to 5 inches wide. Moreover, the flexible material and or the size and shape of the cover 120 or the parts of the cover may be chosen so that the cover 120 can be folded easily with one hand. The shape of the cover 120 may include rounded edges 107 and a rounded bottom 105, which may make it easier to fold the cover 120. In some embodiments, the length may be larger than the width, which may also make it easier to fold the cover 120. In some embodiments, the cover 120 may have a uniform thickness. In some embodiments, the cover 120 may be thicker in certain areas than in other areas. For example, the cover 120 may have a thicker bottom 105. In some embodiments, the sides 104 of the cover 120 may be thicker. In some embodiments, a strip of material in the bottom and sides of the cover 120 may connect the recesses 122, 123 and may be thinner to make it easier to fold the cover 120.

The cover 120 may include more than two recesses or may only include one recess. In some embodiments, there may be more than one tab 124 in the opposing recess 123. In some embodiments, there may be one or more tabs in other recesses. The tabs may be any appropriate shape. For example, the tabs may be rectangular, semispherical, curved, triangular, hexagonal, or any other appropriate shape.

Figure 4:
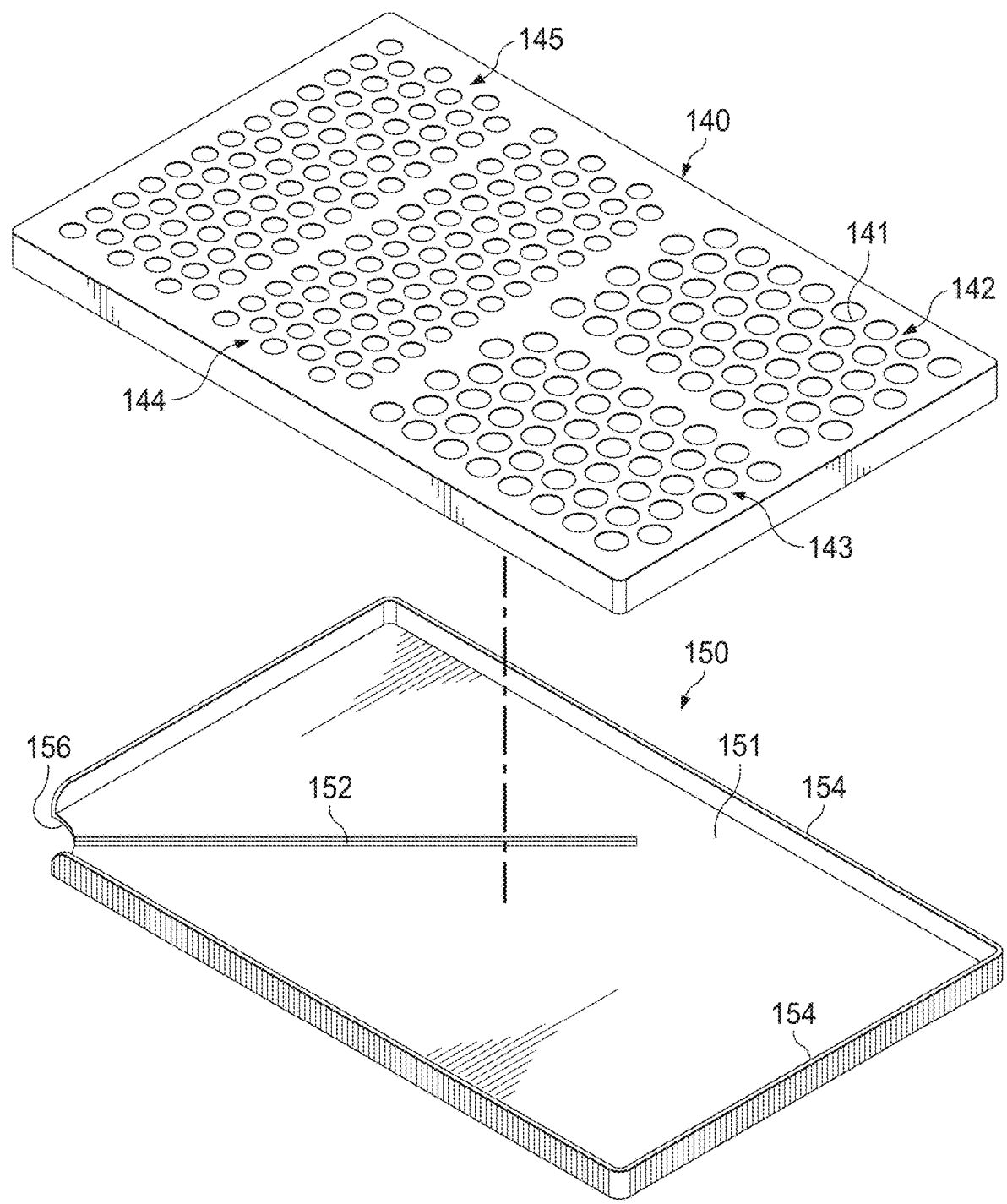
FIG. 4 shows a perspective view of a flexible mold and a backer board of a pellet preparation system, according to aspects of the present disclosure.
Figure 5:
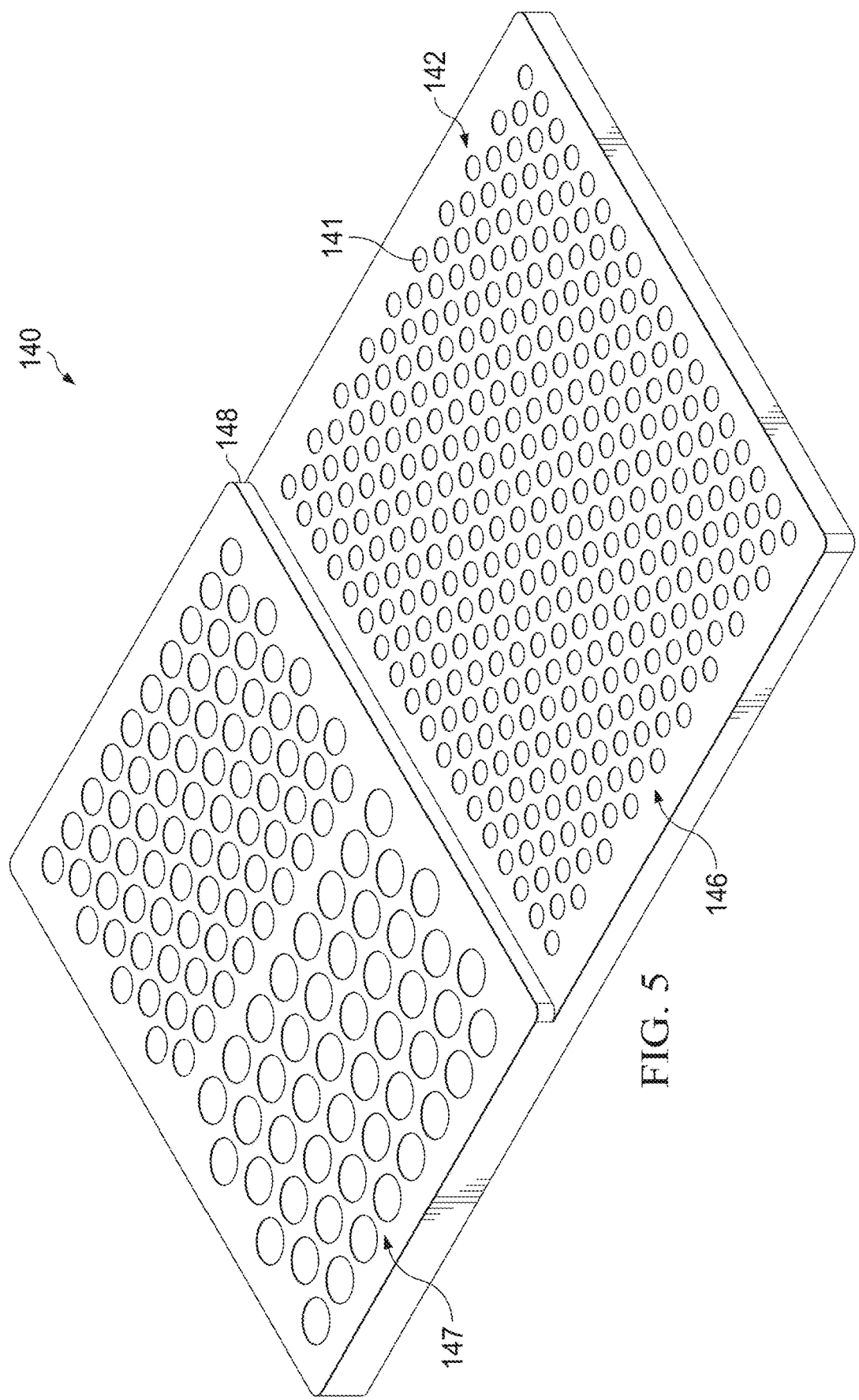
FIG. 5 shows a perspective view of a flexible mold, according to aspects of the present disclosure.
Figure 6:
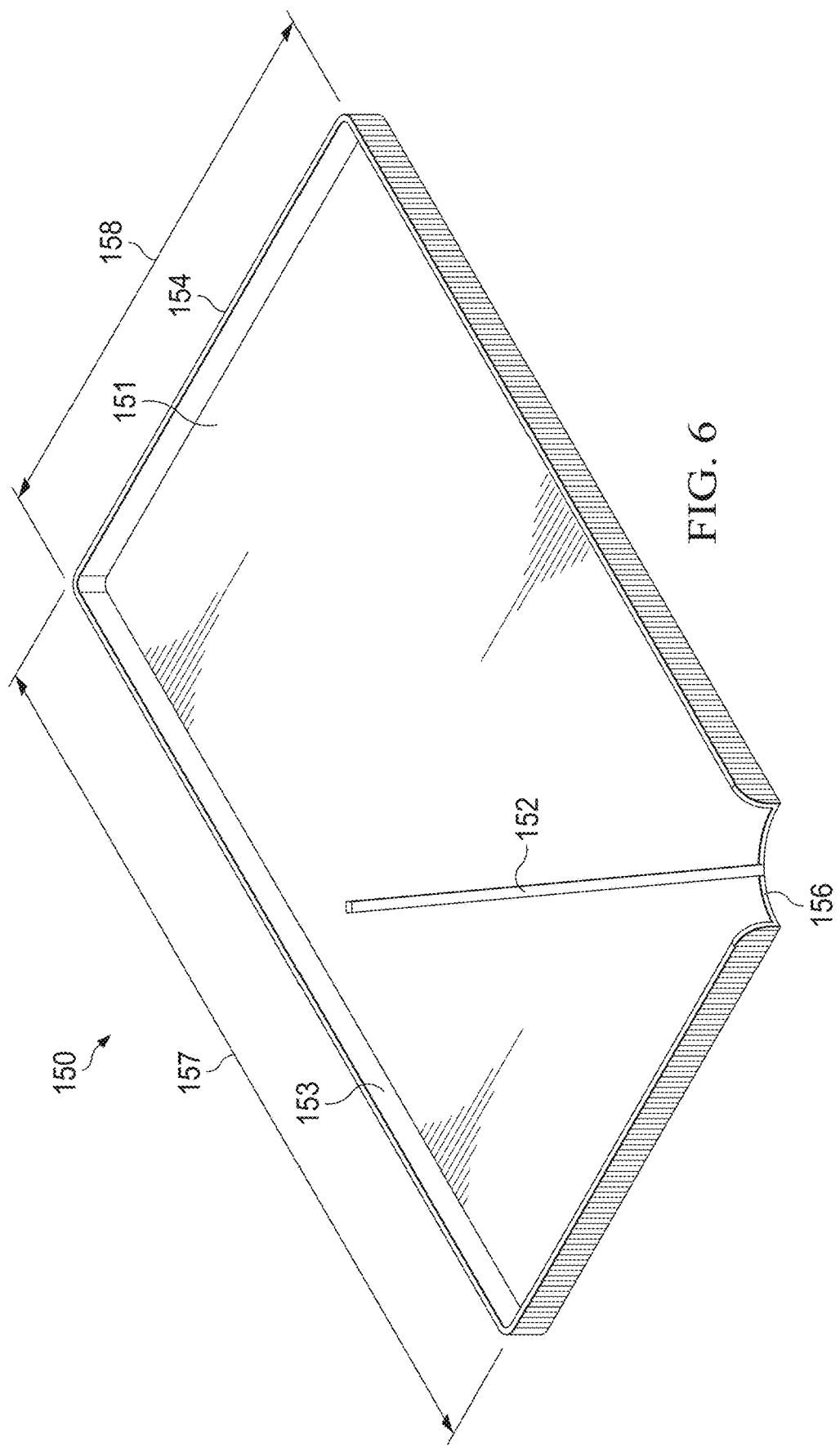
FIG. 6 shows a perspective view of a backer board of a pellet preparation system, according to aspects of the present disclosure.

FIGS. 4, 5, and 6 are perspective view of a flexible mold 140 or mat and a backer board 150 of a pellet preparation system. The pellet preparation system may be included with the kit 100 shown above in FIGS. 1-3. The flexible mold 140 may include a plurality of cavities 141, which may define the shape of the pellets to be formed. In some embodiments, the flexible mold 140 includes cavities having different shapes and/or sizes. For example, the different-shaped cavities may be selectively used by the physician to form pellets of different shapes depending on the application or the preferences of the physician. In the illustrated embodiment, the mold 140 has a first 142, second 143, third 144, and fourth 145 set of cavities. The first 142 and second 143 cavities are larger volume than the third 144 and fourth 145 set of cavities. Moreover, the first 142 and second 143 cavities are arranged width-wise along the mold 140 whereas the third 144 and fourth 145 set of cavities are arranged length-wise. In other embodiments, the mold 140 may have fewer or more sets of cavities than what is shown in FIG. 4. For example, the mold 140 may have a single set of cavities, two sets of cavities, three sets of cavities, five sets of cavities, and/or any other suitable number of sets of cavities. Each set of cavities may correspond to a different pellet size and/or shape, in some embodiments. In other embodiments, two or more of the sets of cavities may correspond to a same pellet size and/or shape.

FIG. 5 shows another embodiment of a flexible mold 140. In the illustrated embodiment, the mold 140 may have a first height at a first set 146 of cavities and a second height at a second set 147 of cavities. The first and second heights may be different such that the first and second set of cavities form pellets of different volumes. For example, in the illustrated embodiment, the first set 146 of cavities has a height that is less than the height of the second set 147 of cavities such that there is a ledge 148 between the two sets 146, 147. Moreover, the first set 146 of cavities has a smaller depth than the second set 147 of cavities. Thus, the first set 146 of cavities has a smaller volume than the second set 147 of cavities. This embodiment is configured such that the first and second set of cavities form pellets of different volumes with different heights. In some aspects, the height of the mold for each set of cavities may correspond to the depth and/or volume of the cavities. The mold 140 is made of flexible material so that the pellets can be removed easily after they have hardened. The stiffness of the mold 140 may be related both to the material properties and the geometry of the mold 140. Because it can be more difficult to remove a pellet from a very stiff mold 140, the mold 140 may have different heights to adjust the stiffness of the mold 140 in different areas so that the height is appropriate to eject the size of pellets molded in that area. For example, it may be advantageous that the mold 140 has a smaller height or thickness for smaller cavities. In this way, the lower rigidity of the mold 140 may facilitate ejection of the pellets from the mold 140. The sets of larger cavity sizes may be in a taller/thicker region of the mold 140 so that the sets 146, 147 are separated by the ledge 148. in some aspects, for pellets with a height of approximately $3/16$ inches, the height of the mold 140 may be in the range of $1/2$ to $5/8$ inches. In other embodiments, for pellets with a height of approximately $1/8$ inches, the height of the mold 140 may be in a range of $5/32$ to $7/32$ inches. In some embodiments, the height of the mold may be in a range of 1.25 to 1.75 times the height of the pellet. In some embodiments, the height of the mold may be in a range of 1.1 to 2 times the height of the pellet. However, the height of the mold and cavities may be any appropriate amount.

In some embodiments, a first set of cavities may be a first shape and a second set of cavities may be a second shape such that pellets of a different shape are formed. The mold 140 may have any appropriate number of different cavities 141 with differing sizes and/or shapes.

In some embodiments, the mold 140 may be manipulated so that pellets from each set of cavities are ejected individually. In some embodiments, the mold 140 may be manipulated so that all of the pellets may be ejected at the same time.

The flexible mold 140 may include silicone, rubber, latex, thermoplastic elastomer, and/or any other suitable material. In some embodiments, the flexible mold 140 comprises the same material as the flexible cover 120. In other embodiments, the flexible mold 140 may include a material that is different from the flexible cover 120. As explained further below, the mixed paste can be worked into the cavities of the mold 140 and left to cure. Once the pellets are cured, the flexible mold 140 can be flexed, bent, folded, twisted, and/or otherwise manipulated to eject the cured pellets from the flexible mold 140.

Referring generally to FIGS. 4 and 6, the backer board 150 includes a flat surface 151 and raised edges 154 around the perimeter of the flat surface 151. When the pellets are ejected from the mold 140, they may be poured onto the backer board 150. The raised edges 154 may contain the pellets after ejection from the mold 140. The flat surface 151 and raised edges 154 may form a basin which is shaped to fit the mold 140 and to hold the pellets when they are ejected from the mold 140.

In some embodiments, there is a cutout 156 or notch at a corner of the backer board 150. The edges 154 of the backer board 150 may extend to the ends of the cutout 156. When the backer board 150 is folded, the backer board 150 may function as a funnel, whereby the backer board 150 can be tilted to direct the pellets toward the cutout 156. In some embodiments, the cutout 156 can be placed, for example, at or near the surgical site to deliver the cured pellets to the surgical site. In other embodiments, the cutout 156 can direct the cured pellets into the flexible cover 120, and the flexible cover 120 may be used to deliver the pellets to the surgical area. The cutout 126 is sized and shaped to allow the pellets to be poured out of the backer board 150 in a controlled manner. In some embodiments, the backer board 150 may not have a cutout 156 and instead the pellets may be funneled over the edge 154 or corner of the backer board 150.

In the illustrated embodiment, the backer board 150 includes four edges 154. However, the backer board 150 may include any appropriate number of edges 154. For example, the backer board 150 may include 1, 2, 3, 4, 5, 6, 7, 8, 9, or 10 edges 154. The edges 154 may extend around a majority of the perimeter of the backer board 150. In some embodiments, the edges 154 may not extend around the entire perimeter of the backer board 150 and there may be gaps between one or more edges 154 of the backer board 150 while having an interference fit with the mold 140. For example, there may be three edges 154 that form an interference fit with the mold 140.

In some embodiments, the backer board 150 also includes a relief 152 or groove formed in the flat surface 151. The relief 152 includes a narrow region of thinned material which allows the backer board to flex, fold, bend, and/or otherwise deform about the relief 152. Accordingly, the relief 152 may improve the function of the backer board 150 as a funneling or delivery device for the pellets. The relief 152 may be comprised of the same material as the rest of the backer board 150 or may be made of a more flexible material. In some embodiments, the relief 152 may comprise a material that is different from and more flexible than the material of the rest of the backer board 150. In some embodiments, the relief 152 may be the same height as the rest of the flat surface 151 of the backer board 150 and may be comprised of the more flexible material. In some embodiments, the relief 152 may not include a thinned region of material, and rather may be the same thickness as the rest of the backer board 150 base.

Figure 7:
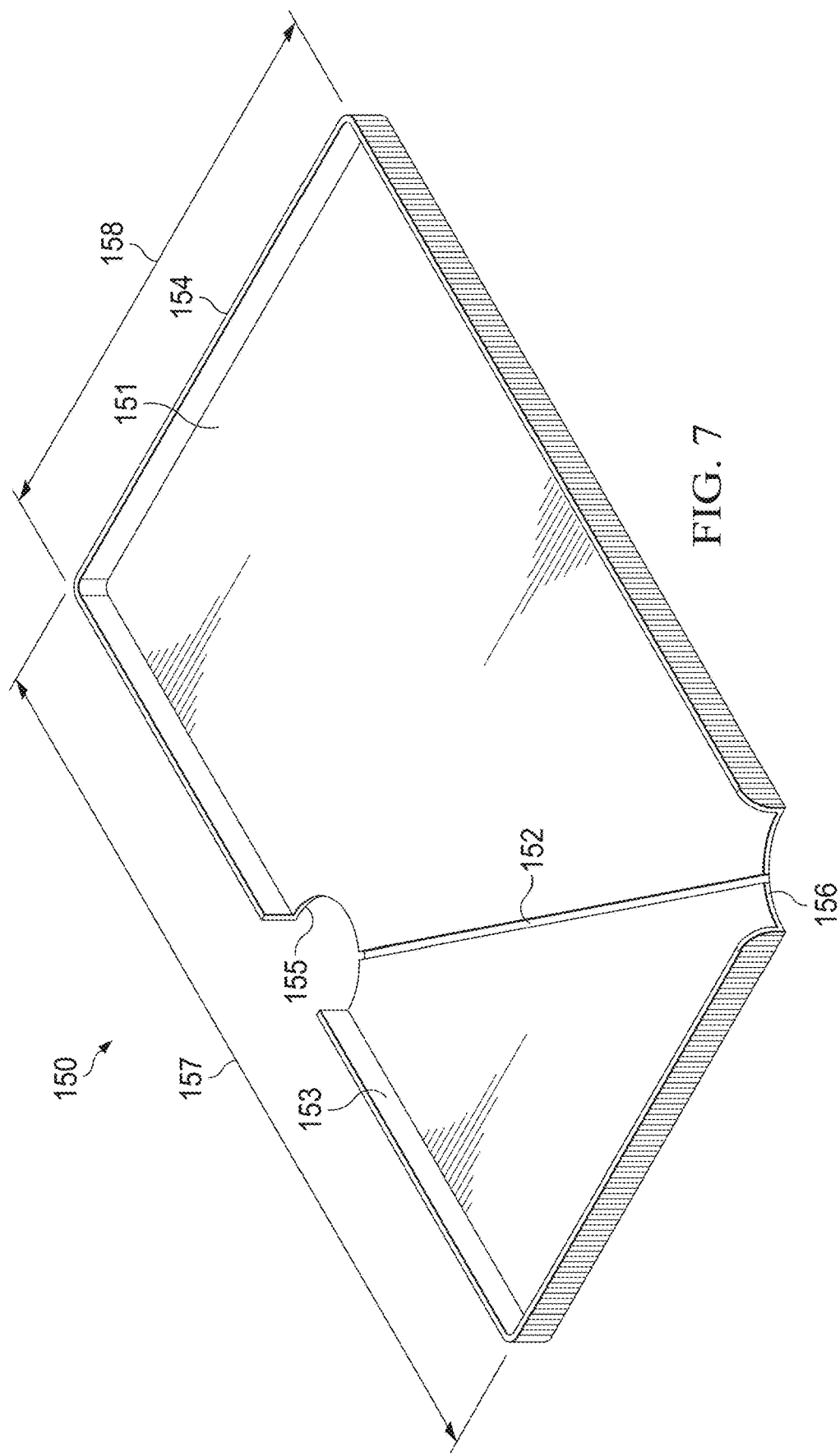
FIG. 7 shows a perspective view of a backer board of a pellet preparation system, according to aspects of the present disclosure.

In the embodiment illustrated in FIGS. 4 and 6, the relief 152 extends from the cutout 156 towards an opposite edge 153 of the backer board 150 without contacting the opposite edge 153. However, in some embodiments, the relief 152 may extend from the cutout 156 to the opposite edge 153 as illustrated in FIG. 7. In this illustrated embodiment, the backer board 150 has a second opposing cutout 155 on the opposite edge 153 at the end of the relief 152. This may allow the backer board 150 to bend more easily or bend more deeply about the relief 152 because the opposite edge 153 does not limit the degree of bending.

In other embodiments, the backer board 150 may not have a relief 152 and may include a material that is flexible enough to allow it to bend. In some embodiments, the backer board 150 may have more than one relief, including, for example, 2, 3, 4, or 5 reliefs.

The backer board 150 may provide for some rigidity and support for the flexible mold 140. For example, a physician may prefer to hold the flexible mold 140 in her hand while working the paste into the cavities of the flexible mold 140. Accordingly, the backer board 150 provides a flat and rigid rear support for the flexible mold 140 so that the flexible mold 140 does not inadvertently flex or move while working the paste into the mold 140 or while the paste is curing to a hard pellet form. Thus, the backer board 150 may include a material that is more rigid than the material of the mold 140. For example, the backer board 150 may include polyethylene, ABS (acrylonitrile butadiene styrene), acetal polymer (polyoxymethylene), aluminum alloy, titanium alloy, or steel. In some embodiments, the backer board 150 may include a material that is more rigid than the material of the mold 140, but that is flexible enough so that the backer board 150 may be bent. For example, it may take 1 inch-pound or more to deflect the backer board 150 $\frac{1}{100}$ inches, while the mold 140 may deflect an inch with 1 inch-pound or less of moment. The backer board 150 may have a different rigidity along a first axis than along a second axis. For example, the backer board may be more rigid along a longitudinal axis than along an axis coaxial with the relief 152.

Additionally, the edges 154 may provide additional rigidity to the backer board 150. The edges 154 and the flat surface 151 of the backer board 150 may include the same material, the material of the edges 154 may be more rigid than the material of the flat surface 151, or the material of the flat surface 151 may be more rigid than the material of the edges 154. The edges 154 may be thicker, thinner, or the same thickness as the flat surface 151.

The edges 154 may be any appropriate height. The edges 154 may be the same height or may be different heights. For example, the edges 154 around the cutouts 156, 155 may be thinner, which may make it easier to bend the backer board 150.

In some embodiments, the edges 154 extend orthogonally from the flat surface 151. In some embodiments, the edges 154 are angled outward or inward from the vertical forming a non-orthogonal angle with the flat surface 151. In some embodiments, the edges 154 may be angled outward from the vertical, which may make it easier to facilitate the insertion and seating of the mold 140 into the backer board 150.

Further, as mentioned above, the backer board 150 may be used as a temporary container to catch and hold the cured pellets from the flexible mold 140. However, in some instances, the physician may eject the cured pellets from the mold 140 directly into the flexible cover 120.

In some embodiments, the backer board 150 may be sized and shaped so that a user can hold it with one hand. The backer board has a length 157 and a width 158. The dimensions 157, 158 may be any appropriate value, but preferably may be chosen so that the backer board 150 is easy to handle. For example, the length 157 may be 4 inches to 12 inches and the width may be 4 inches to 12 inches. In a particular embodiment the length 157 may be 4 inches and the width 158 may be 6 inches.

Figure 8:
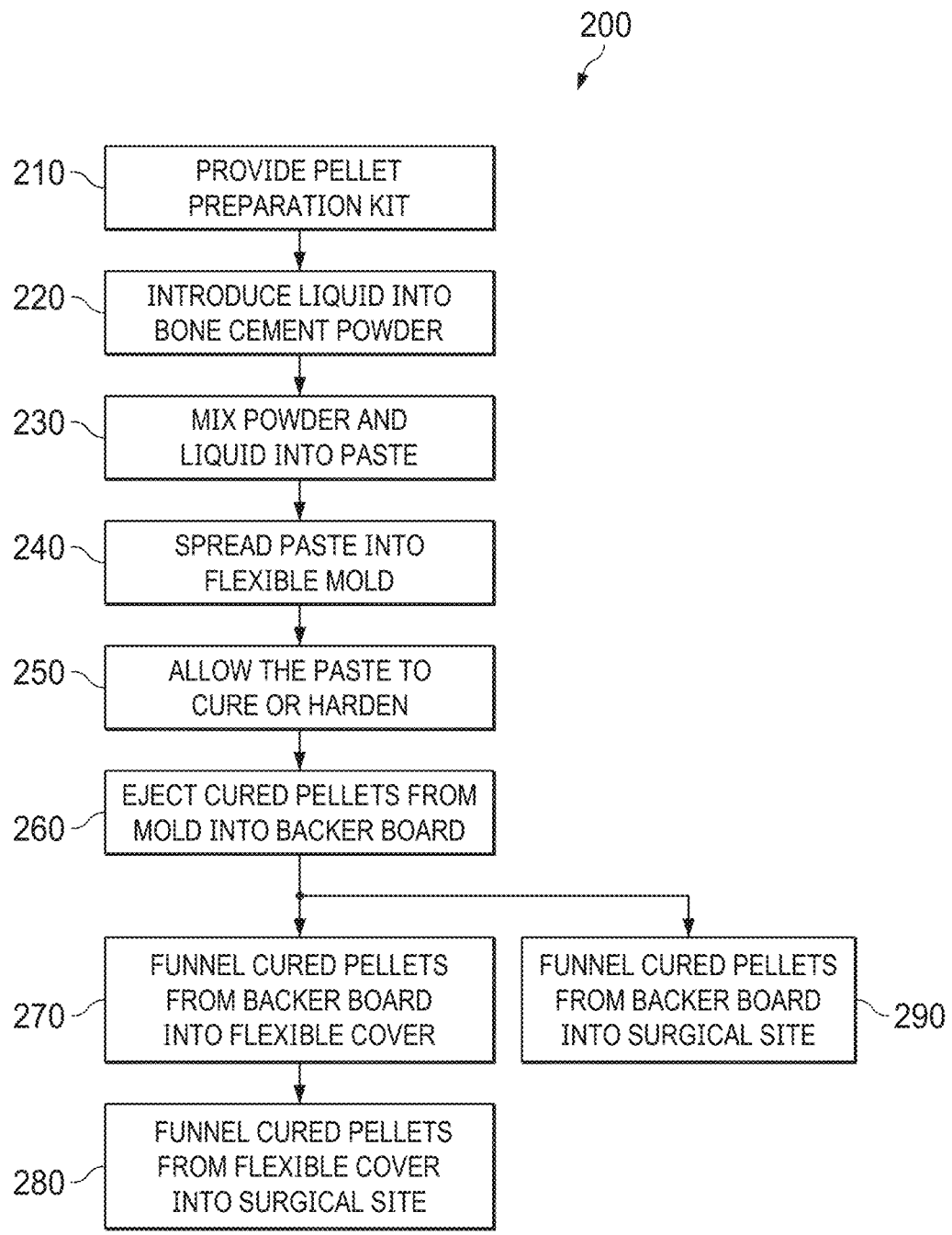
FIG. 8 is a flow diagram of a method for preparing therapeutic pellets, according to aspects of the present disclosure.

FIG. 8 is a flow diagram of a method 200 for preparing therapeutic pellets 180 in accordance with an embodiment of the present disclosure. The method 200 may be performed using one or more of the devices, kits, systems, and/or other components described above with respect to FIGS. 1-7, for example. FIGS. 9A-9H illustrate various steps of the method 200. In some embodiments, the method 200 may be used to form bone cement pellets 180 used for one or more therapeutic procedures, including for example, an orthopedic surgery. In some embodiments, the therapeutic pellets 180 may include or incorporate antibiotic materials to prevent, cure, and/or otherwise control infection in a surgical site. For example, the pellets 180 may include calcium sulfate and/or calcium phosphate along with vancomycin and/or tobramycin.

Referring to FIG. 8, at step 210, a pellet preparation kit 100 is provided. The pellet preparation kit 100 may include, for example, the bowl 110, the cover 120, and the liquid 130 shown in FIG. 1 above. In some embodiments, the bowl 110 contains a powder 111, such as, for example, calcium sulfate powder. The powder 111 may come pre-packaged in the bowl 110 with the lid 112 closed to simplify the mixing process. The pellet preparation kit 100 may further include one or more tools, such as spreading tools, mixing tools, and/or any other suitable tool. In some embodiments, step 210 further includes providing a flexible mold 140. The mold 140 may include one or more cavities 141 for forming the pellets. Step 210 may further include providing a backer board 150 configured to couple to the mold 140. The backer board 150 may be sized and shaped to support and retain the mold 140 inside the backer board 150. In some embodiments, the backer board 150 may include a flat surface 151 and raised edges 154 or side walls around the perimeter of the flat surface 151.

Figure 9A:
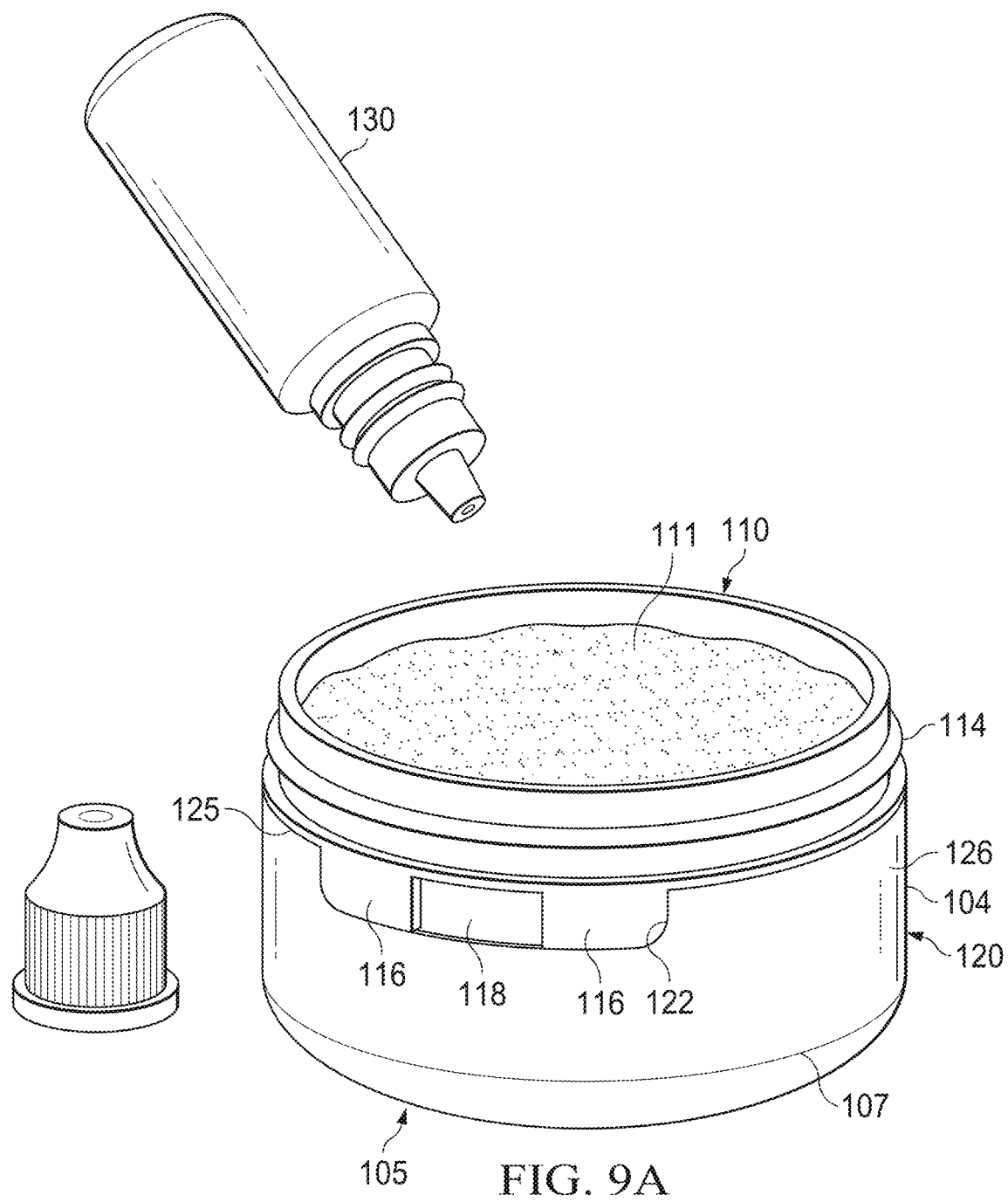
FIGS. 9A-9H illustrate various steps of the method of FIG. 5, according to aspects of the present disclosure.

Referring to FIGS. 8 and 9A, at step 220, a liquid 130 is introduced into the powder 111 contained within the bowl 110. In this step 220, the lid 112 may be removed from the bowl 110 to expose the powder 111 within the bowl 110. Then the liquid 130 may be added to the powder 111 by pouring or dropping the liquid 130 into the bowl 110. In some embodiments, the liquid 130 may be a water-based solution, and the powder 111 may be a calcium-based salt such as calcium sulfate or calcium phosphate. In alternative embodiment, the liquid 130 may include a monomer liquid, and the powder 111 may include a copolymer configured to react with the liquid monomer.

Figure 9B:
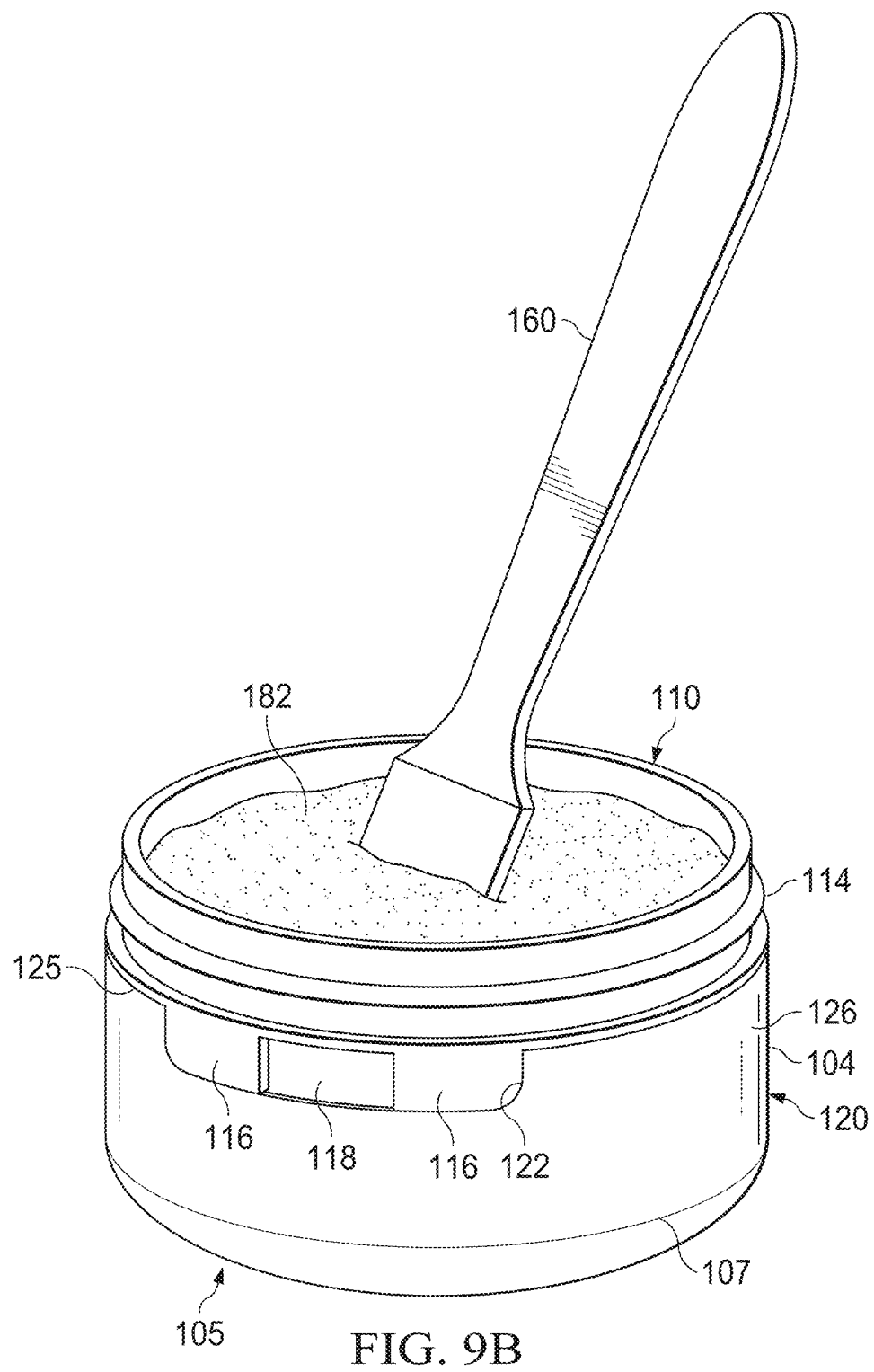

Referring to FIGS. 8 and 9B, at step 230, the powder 111 and liquid 130 are mixed into a paste 182 within the bowl 110. The mixing may be performed using a mixing tool 160. The mixing tool 160 may include a spatula, mixing knife, whisk, and/or any other suitable tool. The mixing may be performed over a period of time. In some aspects, the flexible cover 120 may provide for improved grip of the bowl 110 so that the physician or technician can hold both the bowl 110 in one hand and the mixing tool 160 in the other hand.

Figure 9C:
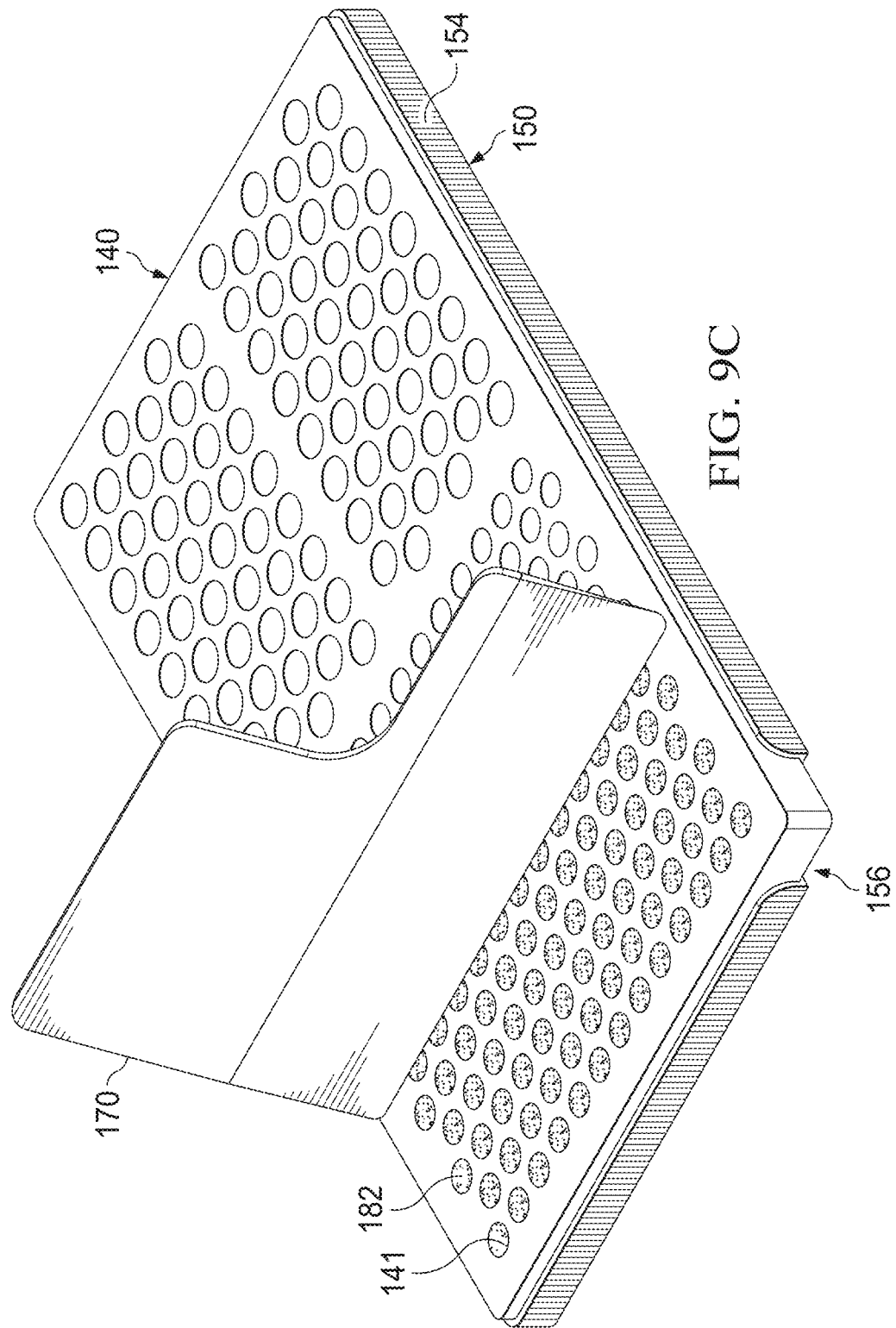

Referring to FIGS. 8 and 9C, at step 240, the paste 182 produced from step 230 is spread into a flexible mold 140. In the illustrated embodiment, the paste 182 is spread into the mold 140 using a spreading tool 170. The spreading tool 170 includes a straight, flat surface that can be dragged along the surface of the mold 140 to work the paste 182 into the individual cavities of the mold 140. In some embodiments, the size (e.g., width, length) of the spreading tool 170 may correspond to a size (e.g., width, length) of the mold 140. Similar to the mixing procedure of step 230, the physician may desire to hold the mold 140 in her hand while spreading the paste into the mold 140. Accordingly, a backer board 150 is provided to support the mold 140. The backer board 150 may include a flat surface that is rigid along at least one axis. Accordingly, the backer board 150 may prevent the mold 140 from bending or flexing during the spreading process of step 240 and during the subsequent curing.

Once the paste 182 has been removed from the bowl 110, the cover 120 can be removed from the bowl 110 and set aside. The cover 120 is now a container ready to hold the cured pellets 180. As described in more detail below To work the paste down to the bottom of the cavities, the mold 140 and backer board 150 can be tapped to release any trapped air under the paste and to aid gravity in getting the paste to the bottom of the cavity 141. Spreading and tapping can be alternated until the cavities 141 are properly filled.

Referring to FIG. 8, in step 250, the pellets are allowed to cure or harden. After the paste is spread into the mold 140, the paste may require time to cure or harden. The liquid 130 and the powder 111 that are mixed together to form the paste, may be configured to chemically harden or cure over a period of time. Thus, step 250 includes waiting for the paste to cure or harden so that the pellets 180 can form. The mold 140 and backer board 150 can be set down and the paste 182 can be left stable until it has completed curing to a hard state. This step 250 may take any appropriate amount of time, including for example, 1 minute, 4 minutes, 5 minutes, 10 minutes, 30 minutes, 60 minutes, or 90 minutes.

For example, in some embodiments, the curing time may be in a range of 4 minutes to 60 minutes. It may be desirous or beneficial to avoid disturbing the paste 182 while it is curing in the mold 140. Flexing the mold 140 during the curing process may cause the pellets 180 to fracture and prevent them from forming into hard, solid pellets 180. The backer board 150 keeps the mold 140 from flexing. Once the pellets 180 have cured, the backer board 150 can be removed from the mold 140.

Figure 9D:
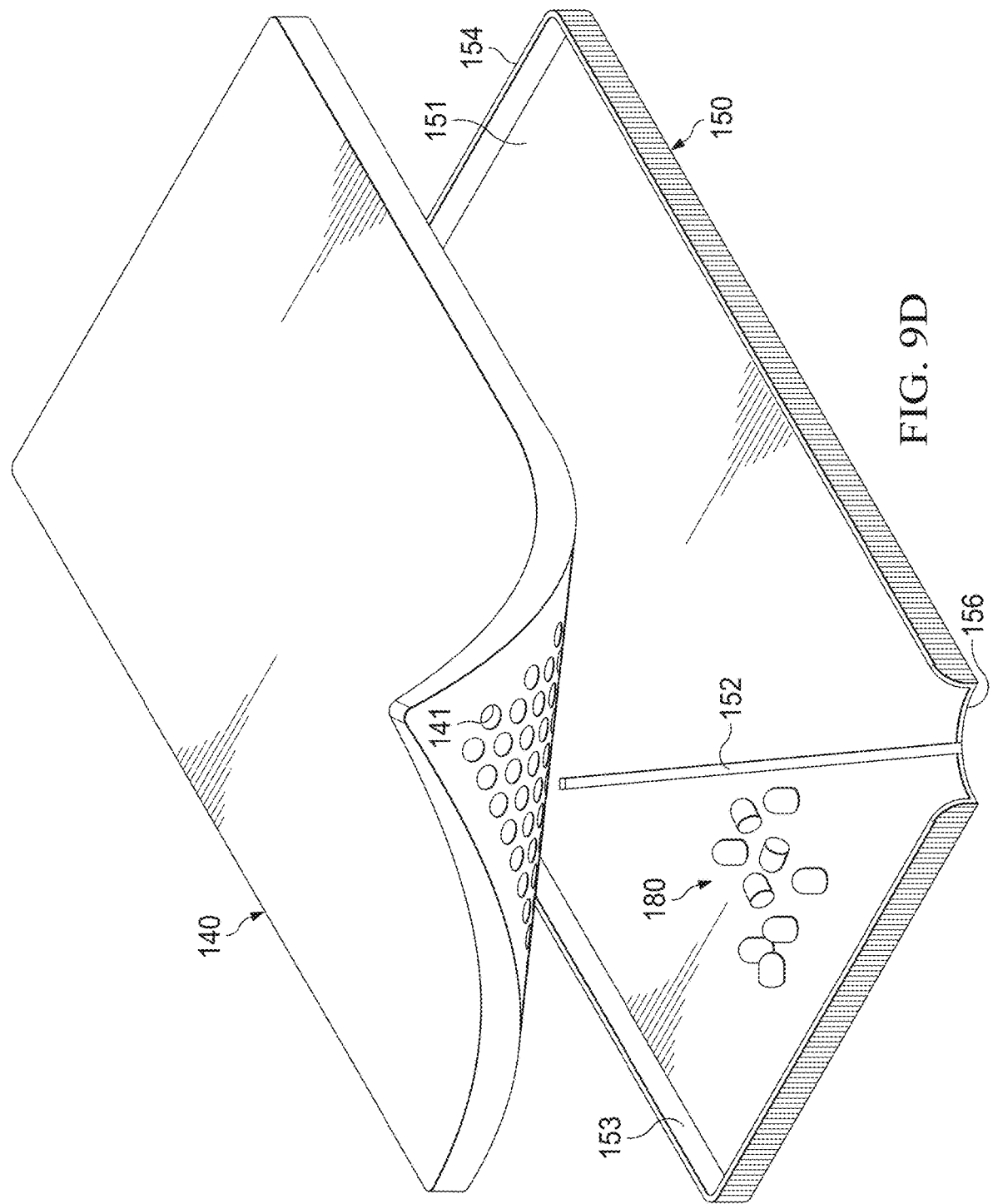

Referring to FIGS. 8 and 9D, at step 260, the cured pellets are ejected from the cavities 141 of the mold 140 into the backer board 150. Step 260 may include bending, flexing, tapping, stretching, or otherwise manipulating the mold 140. The backer board 150 includes a plurality of raised surfaces or edges 154 so that when the pellets 180 are ejected onto the backer board 150, the edges 154 prevent the pellets 180 from moving off of the backer board 150 onto other surfaces in the surgical environment. The raised surfaces 154 may also add stiffness to the backer board 150.

Referring to FIG. 8, the method 200 includes two ways in which the surgeon can deliver the pellets 180 to the surgical site. In steps 270 and 280, the surgeon may use the flexible cover 120 to deliver the pellets to the surgical site. Alternatively, in step 290, the surgeon may use the backer board 150 itself to deliver the pellets 180 to the surgical site without using the cover 120 as an intermediary container.

FIGS. 9E-9H illustrate how the flexible cover 120 may be used to deliver pellets 180 to the surgical site according to steps 270 and 280 of FIG. 8. In these embodiments, the flexible cover 120 has been removed from the bowl 110.

Figure 9E:
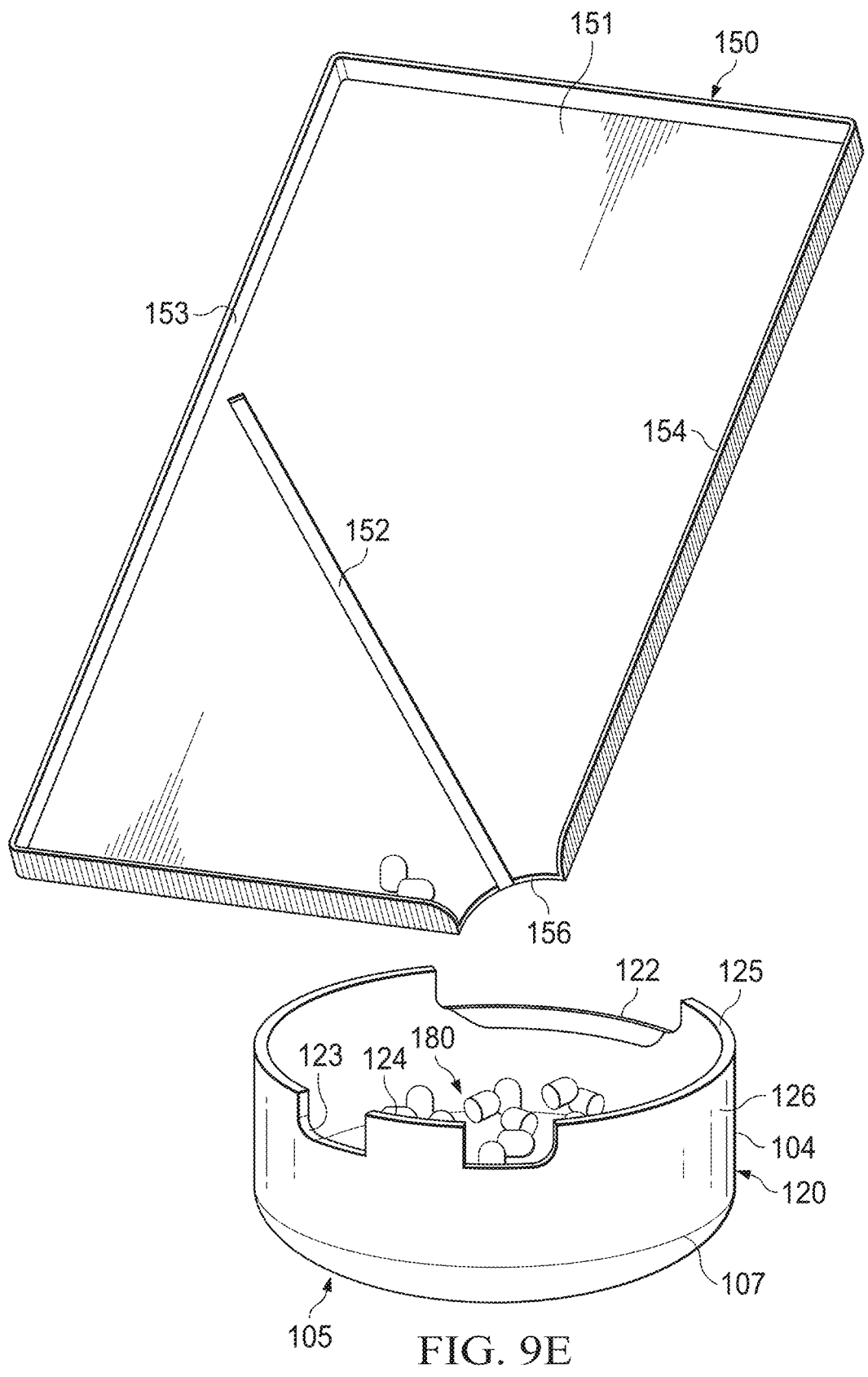

At step 270 of FIG. 8, the pellets 180 are directed from the backer board 150 into the cover 120. FIG. 9E illustrates the same embodiment of the backer board 150 shown in FIGS. 4, 6, and 9D. In the illustrated embodiment, the backer board 150 has a cutout 156 at one corner and a relief 152 formed in the flat surface 151 extending from the cutout 156 towards the opposite edge 153 of the backer board 150 across from the cutout 156. The relief 152 may not contact the opposite edge 153. However, in some embodiments, the relief 152 may reach the opposite edge 153. The relief 152 may be an area of thinned material, which makes it easier for the backer board 150 to bend along the relief 152 and funnel the pellets 180 towards the cutout 156 and into the flexible cover 120.

Figure 9F:
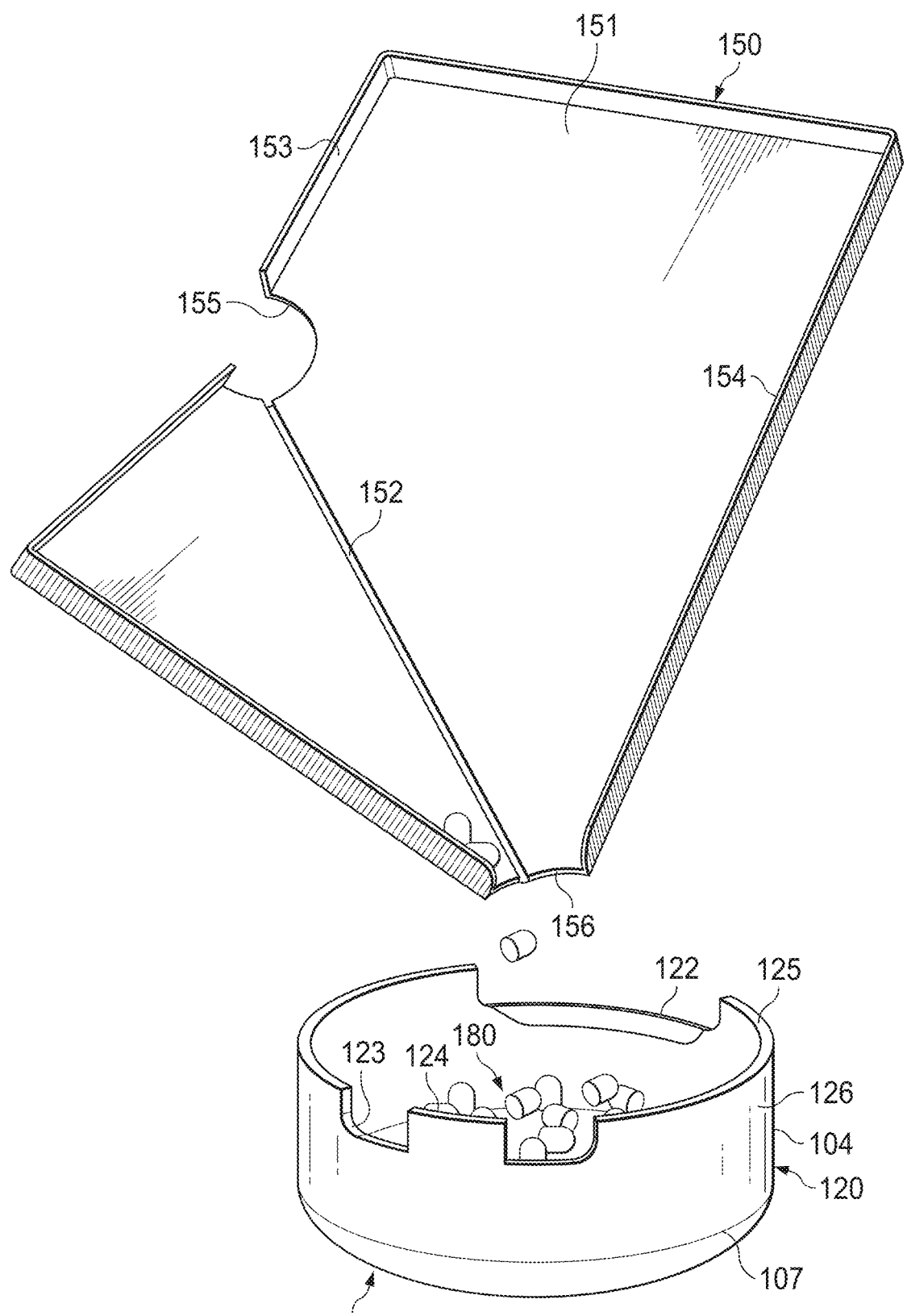

FIG. 9F illustrates another embodiment of the backer board 150, which is also illustrated in FIG. 7. In this embodiment, the backer board 150 has a cutout 156 on the corner of the backer board 150 and a second opposing cutout 155 on the opposite edge 153 from the corner cutout 156. There may be a relief 152 that extends between the cutouts 155, 156. This embodiment of the backer board 150 may be easier to bend because there are two cutouts 155, 156 connected by a relief 152. By incorporating a second cutout, the backer board 150 is able to bend more fully because it is not restricted by the opposite edge 153. Thus, this embodiment may more easily funnel the pellets 180 into the flexible cover 120.

Figure 9G:
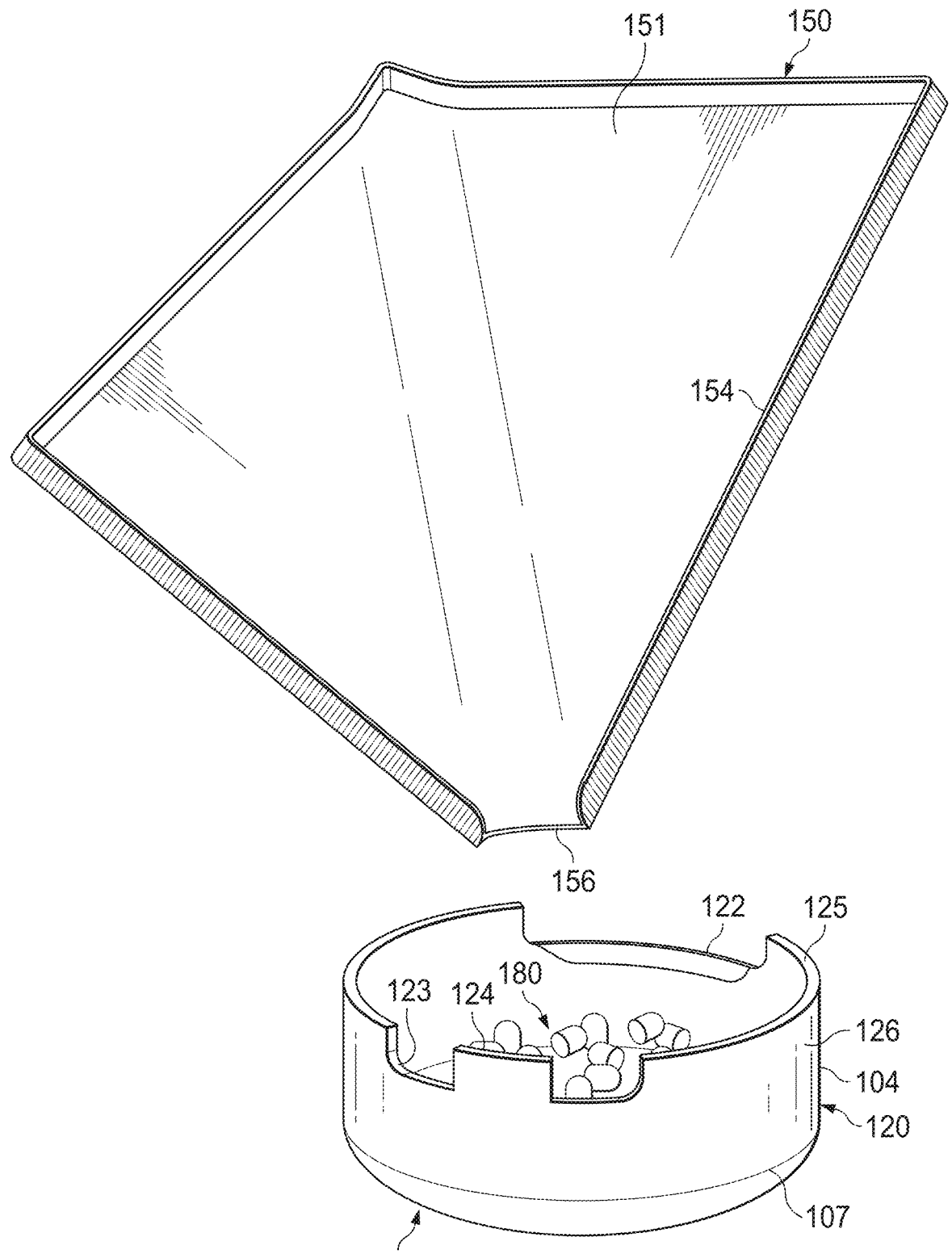

FIG. 9G illustrates yet another embodiment of the backer board 150. In this embodiment, the backer board 150 has a cutout 156 on the corner, but does not have a relief 152 formed in the flat surface 151. The backer board 150 may be configured such that the material and thickness of the backer board 150 is significantly stiffer than the mold 140, but is not too stiff to be manually bent so as to funnel the pellets 180 towards the cutout 156. This embodiment may be easier to manufacture than the backer board 150 embodiments shown in FIGS. 9E and 9F because it does not require a relief 152 or an extra cutout 155 to be formed.

In any of the embodiments shown or described in reference to FIGS. 9E-9G, the backer board 150 may be held in one hand and may be bent using only that one hand so that the surgeon can easily funnel the pellets 180 into the cover 120. When the backer board 150 can be handled one-handed, the surgeon has one hand free to hold the cover 120 or perform another task. In some embodiments, the backer board may require two hands to bend the board, which may cause the board material to yield and permanently deform into the funnel shape.

Figure 9H:
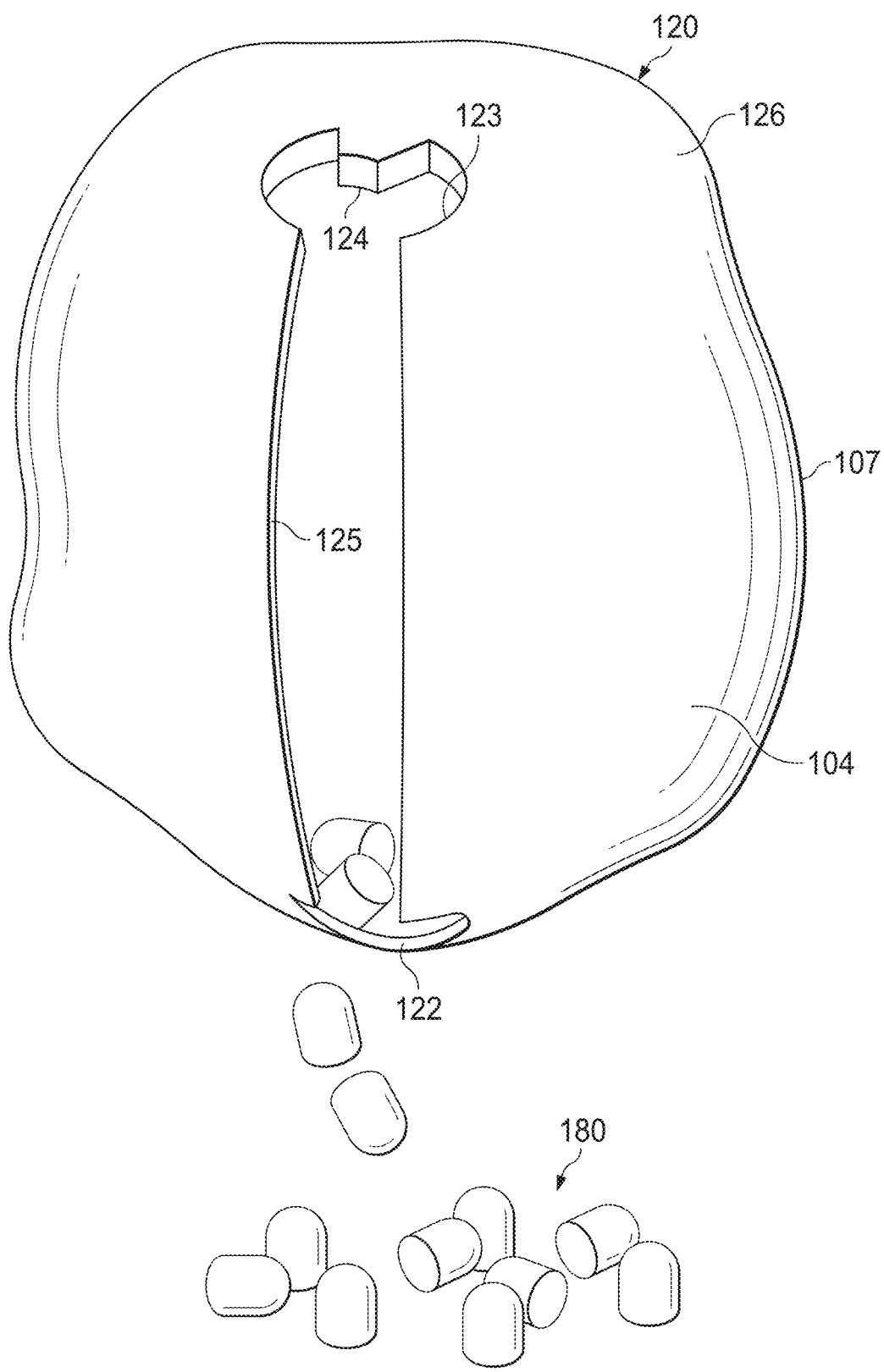

Referring to FIGS. 8 and 9H, at step 280, the cover 120 is in a folded configuration and is used to funnel pellets 180 to the surgical site. As described above in reference to FIG. 3, the flexible cover 120 may have pouring recess 122 and an opposing recess 123 opposite the pouring recess 122. The cover 120 may be folded along the recesses 122, 123 such that the sides of the rim 125 come together with the recesses 122, 123 on the ends, forming a lemon-like shape. The pouring recess 122 may form an opening that the pellets 180 may be poured or funneled out of into the surgical site. The opposing recess 123 may help the cover 120 to bend to improve pouring of the pellets 180. The opposing recess 123 may also include a tab 124 that extends from the recess 123. The tab 124, in addition to helping the cover 120 attach to the bowl 110, may prevent the cover 120 from bending too much. Thus, the tab 124 may allow the pouring recess 122 to form a larger opening, which may make it easier for the surgeon to pour out the pellets 180 to deliver them to the surgical site.

The surgeon may hold the cover 120 in one hand and may use only that hand to fold the cover 120, thus allowing the surgeon to deliver the pellets 180 to the surgical site with one hand. By allowing the cover 120 to be handled one handed, the surgeon has one hand free to perform other tasks.

Referring to FIG. 8, at step 290, instead of delivering the pellets 180 from the backer board 150 to the cover 120 and then to the surgical site, the pellets 180 may be delivered directly from the backer board 150 to the surgical site. Any embodiment of the backer board 150 may be bent as described above in reference FIGS. 9E-9G. However, instead of funneling the pellets 180 into the cover 120, the pellets 180 are funneled into the surgical site.

Persons of ordinary skill in the art will appreciate that the implementations encompassed by the present disclosure are not limited to the particular exemplary implementations described above. In that regard, although illustrative implementations have been shown and described, a wide range of modification, change, combination, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

The invention claimed is:

1. A system for forming therapeutic pellets, the system comprising:
    an elastomeric mold defining one or more cavities;
    a backer board removably coupled to the elastomeric mold, wherein the backer board comprises:
        a flat surface;
        two or more raised edges extending upward from the flat surface, wherein the flat surface and the two or more raised edges form a flat basin which is shaped to rigidly support and fit around the elastomeric mold; and
        a relief configured to facilitate bending of the backer board about the relief;
    wherein the backer board is formed of a first material comprising a first rigidity, wherein the elastomeric mold is formed of a second material comprising a second rigidity that is less than the first rigidity; and
    wherein the backer board supporting the elastomeric mold within the flat basin is configured to be supportable by one hand of a user.

2. The system of claim 1, the backer board further comprising a first cutout at a corner of the backer board, and wherein the relief is oriented toward the first cutout.

3. The system of claim 2, wherein the relief comprises a first end disposed proximal to the first cutout and a second end at a side of the backer board.

4. The system of claim 3, the backer board further comprising a second cutout located at the second end of the relief on the side of the backer board.

5. The system of claim 1, wherein the relief is thinner than the flat surface.

6. The system of claim 1, wherein the backer board comprises:

a width in a range of 2 to 6 inches; and, a length in a range of 3 to 12 inches.

7. The system of claim 1, wherein the two or more raised edges of the backer board are sized and shaped to provide an interference fit with the elastomeric mold to grip the elastomeric mold.

8. The system of claim 7, wherein the two or more raised edges of the backer board are configured to fit around a perimeter of the elastomeric mold.

9. The system of claim 7, wherein the elastomeric mold is formed of a silicone rubber.

10. The system of claim 7, wherein the one or more cavities are configured to hold a paste during a curing process to form the therapeutic pellets.

11. The system of claim 7, wherein the elastomeric mold comprises a first set of cavities and a second set of cavities, wherein a volume of each cavity in the first set of cavities is greater than a volume of each cavity in the second set of cavities.

12. The system of claim 11, wherein the elastomeric mold comprises a first height at the first set of cavities and a second height at the second set of cavities, wherein the first height is greater than the second height, and wherein the elastomeric mold comprises a first depth for each of the first set of cavities and a second depth for each of the second set of cavities, wherein the first height is proportional to the first depth, and wherein the second height is proportional to the second depth.

13. The system of claim 12, wherein the first height is in a range of 1.25 to 1.75 times the first depth, and wherein the second height is in a range of 1.25 to 1.75 times the second depth.

14. A system for forming therapeutic pellets comprising:

a mold formed of a flexible material comprising a plurality of cavities sized and shaped to form the therapeutic pellets, wherein the mold is elastically flexible to expel the therapeutic pellets after a curing process, a backer board formed of a rigid material more rigid than the flexible material, wherein the mold fits within the backer board so that the system can be held by hand during the curing process such that the backer board prevents elastic flexing of the mold, wherein the backer board is separable from the mold and comprises a basin for catching the therapeutic pellets after the curing process and when the mold is elastically flexed to expel the therapeutic pellets, and wherein the backer board comprises a relief groove extending across at least a portion of the basin such that the backer board is foldable along the relief groove to form a dispensing funnel for the therapeutic pellets.

* * * * *